United States Patent
Fontaine et al.

(10) Patent No.: US 6,344,470 B1
(45) Date of Patent: Feb. 5, 2002

(54) AMINOTHIAZOLE DERIVATIVES, METHOD OF PREPARATION AND PHARMACEUTICAL COMPOSITIONS CONTAINING SAME

(75) Inventors: Evelyne Fontaine, Castanet-Tolosan; Danielle Gully, Muret; Pierre Roger, Montigny le Bretonneux; Camille Georges Wermuth, Strasbourg, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/269,516

(22) PCT Filed: Oct. 7, 1997

(86) PCT No.: PCT/FR97/01788

§ 371 Date: Apr. 2, 1999

§ 102(e) Date: Apr. 2, 1999

(87) PCT Pub. No.: WO98/15543

PCT Pub. Date: Apr. 16, 1998

(30) Foreign Application Priority Data

Oct. 8, 1996 (FR) .............................. 96 12256

(51) Int. Cl.[7] .............................. A61K 31/425
(52) U.S. Cl. ...................... 514/370; 548/190
(58) Field of Search ................. 548/190; 514/370

(56) References Cited

U.S. PATENT DOCUMENTS

| | | |
|---|---|---|
| 5,189,049 A | 2/1993 | Frehel et al. |
| 5,378,706 A | 1/1995 | Biziere et al. |
| 5,464,847 A | 11/1995 | Courtemanche et al. |
| 5,470,855 A | 11/1995 | Bernat et al. |
| 5,602,132 A | 2/1997 | Roger et al. |
| 5,856,347 A | 1/1999 | Hashiguchi et al. |

FOREIGN PATENT DOCUMENTS

| | | |
|---|---|---|
| EP | 0 205 069 | 12/1986 |
| GB | 2 022 085 | 12/1979 |
| WO | WO94/01423 | 1/1994 |
| WO | WO97/00868 | 1/1997 |

OTHER PUBLICATIONS

T. N. Birkinshaw et al., "2-(N-N-Disubstituted Amino)thiazoles with Electron-withdrawing Groups at Position 5: Preparation and Investigation of Structural Features", *J. Chem. Soc. Perkin Trans. I*, 1984, 2, 147–153.

D. W. Gillon et al. "N–N–Disubstituted 2–Aminothiazole–5–carbaldehydes: preparation and Investigation of Structural Features", *J. Chem. Soc. Perkin Trans. I*, 1983, 2, 341–347.

*Primary Examiner*—Robert Gerstl
(74) *Attorney, Agent, or Firm*—Michael D. Alexander

(57) ABSTRACT

The subject of the invention is the compounds of formula:

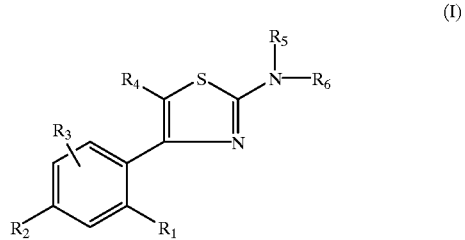

(I)

in which $R_1$, $R_2$, $R_3$, $R_4$, $R_5$ and $R_6$ are as defined in Claim 1.

The compounds have a high affinity for CRF receptors.

5 Claims, No Drawings

AMINOTHIAZOLE DERIVATIVES, METHOD OF PREPARATION AND PHARMACEUTICAL COMPOSITIONS CONTAINING SAME

The subject of the present invention is new branched amino derivatives of thiazole, a process for preparing them and pharmaceutical compositions containing them. These new thiazole derivatives are endowed with CRF (corticotropin releasing factor) antagonizing activity and can therefore constitute active ingredients in pharmaceutical compositions.

Corticotropin releasing factor (CRF) is a peptide whose sequence of 41 amino acids has been characterized by Vale W. et al. in 1981 (Science, 1981, 213, 1394–1397). CRF is the principal endogenous factor involved in the regulation of the hypothalamohypophysoadrenal axis (release of the adrenocorticotropic hormone: ACTH) and its pathologies, as well as in the depressive syndromes which result therefrom, CRF also causes the secretion of β-endorphin, βlipotropin and corticosterone. CRF is therefore the physiological regulator of the secretion of the adrenocorticotropic hormone (ACTH) and more generally of the peptides derived from pro-opiomelanocortin (POMC). In addition to its hypothalamic localization, CRF is widely distributed in the central nervous system, but also in extraneuronal tissues such as the adrenal glands and the testicles. The presence of CRF has also been demonstrated during inflammatory processes.

Numerous animal experiments have shown that the central administration of CRF causes various anxiogenic effects such as the modification of behaviour in general: for example neophobia, reduction in sexual receptivity, decrease in food consumption and lingering sleep in rats. The intracerebroventricular injection of CRF also increases the excitation of the noradrenergic neurons of the locus coeruleus which is often associated, in animals, with a state of anxiety. In rats, the central or peripheral administration of CRF or of related peptides (for example urocortin, sauvagin) induces, in addition to central effects such as an increase in wakefulness and in emotional reactivity towards the surroundings, modifications in the emptying of the stomach, in acid secretion, in intestinal transit and in faecal excretion as well as tensional effects. CRF is also involved in the complex regulation of the inflammatory responses, on the one hand with a pro-inflammatory role in certain animal models, on the other hand as inhibitor of the effects induced by the increase in vascular permeability following the inflammation.

The use of a peptide antagonist, alpha-helical CRF (9-41) (ah-CRF), or of specific antibodies (Rivier J. et al., Science, 1984, 224, 889–891) has made it possible to confirm the role of this peptide in all of these effects. These experiments have also confirmed the important role of CRF in humans in the integration of the complex responses observed during a physiological, psychological or immunological stress both from the neuroendocrinal, visceral and behavioural point of view (Morley J. E. et al., Endocrine Review, 1987, 8, 3, 256–287; Smith M. A. et al., Horm. Res., 1989, 31, 66–71). In addition, clinical data militate in favour of the effective involvement of CRF in numerous disorders resulting from a state of stress (Gulley L. R. et al., J. Clin. Psychiatry, 1993, 54, 1, (suppl.), 16–19) for example:

the existence of the CRF-based test (i.v. administration) in humans has made it possible to demonstrate the modification of the ACTH response in depressive patients (Breier A. et al., Am. J. Psychiatry, 1987, 144, 1419–1425);

the discovery of hypersecretion of endogenous CRF in certain pathologies, for example of a high CRF level in the cephalorachidien fluid in non medicated patients, depressed patients or patients suffering from dementia of the Alzheimer's disease type (Nemeroff C. B. et al., Science, 1984, 226, 4680, 1342–1343; Regul. Pept., 1989, 25, 123–130), or of a reduced density of CRF receptors in the cortex of victims of suicide (Nemeroff C. B. et al., Arch. Gen. Psychiatry, 1988, 45, 577–579);

the dysfunction of the CRF-dependent neurons is even suggested in severe pathologies such as Alzheimer's disease, Parkinson's disease, Huntingdon's chorea and amyotrophic lateral sclerosis (De Souza, E. B., Hospital Practice, 1988, 23, 59).

The central administration of CRF in numerous animal species produces behavioural effects similar to those obtained in man in situations of stress. When they are repeated over time, these effects can cause various pathologies such as fatigue, hypertension, cardiac disorders, modification in the emptying of the stomach, in faecal exretion (colitis, irritable colon), modification in acid secretion, hyperglycaemia, retarded growth, anorexia, neophobia, reproductive disorders, immunosuppression (inflammatory processes, multiple infections and cancers) and various neuropsychiatric disorders (depression, nervous anorexia and anxiety).

The injection, by the intracerebroventricular route, of the reference peptide antagonist, ah-CRF, prevents the effects obtained either by the administration of exogenous CRF, or by the use of stress-causing agents (ether, constraint, noise, electric shock, alcohol withdrawal, surgery) which are capable, by themselves, of inducing an increase in the endogenous CRF level. These results are confirmed by the study of numerous antagonist peptide molecules which are structurally related to CRF and which possess a prolonged duration of action compared with ah-CRF (Rivier J. et al., J. Med. Chem., 1993, 36, 2851–2859; Menzaghi F. et al., J. Pharmacol. Exp. Ther., 1994, 269, 2, 564–572; Hernandez J. F. et al., J. Med. Chem., 1993, 36, 2860–2867). Such CRF-antagonizing peptide compounds are described, for example, in U.S. Pat. Nos. 5,109,111, 5,132,111, 5,245,009 and in Patent Applications WO 92 22576 and WO 96 19499.

In addition, preliminary studies have shown that tricyclic antidepressants could modulate the CRF level as well as the number of CRF receptors in the brain. (Grigoriadis D. E., et al, Neuropsychopharmacology, 1989, 2, 53–60). Likewise, benzodiazepine anxiolytics are capable of reversing the effect of CRF (Britton K. T. et al., Psychopharmacology, 1988, 94, 306), without the mechanism of action of these substances being completely elucidated. These results strengthen, if necessary, the increasing need for molecules which are nonpeptide antagonists of the CRF receptors.

It is important to also report three possible consequences of the states of chronic stress which are immunodepression, fertility disorders as well as the appearance of diabetes.

CRF exerts such effects by interacting with specific membrane receptors which have been characterized in the hypophysis and the brain of numerous species (mice, rats and humans) as well as in the heart, the skeletal muscle (rats, mice) and in the myometrium and the placenta during pregnancy.

A large number of 2-aminothiazole derivatives are already known. Patent Application EP 462 264 describes 2-aminothiazole derivatives whose tertiary amine in the 2 position comprises two substituents each having at least one heteroatom including one amine derivative. These compounds are antagonists of the platelet activating factor (PAF-acether) and find applications in the treatment of asthma, of certain allergic or inflammatory states, of cardiovascular diseases, of hypertension and of various renal pathologies or alternatively as contraceptive agents.

Application GB 2 022 285 describes compounds possessing an activity which regulates the immune response and having anti-inflammatory properties. They are thiazole derivatives which are substituted at the 2 position with secondary amine groups.

Some 2-acylaminothiazole derivatives have been described in Patent Application EP 432 040. These compounds are antagonists of cholecystokinin and of gastrin.

2-Amino-4, 5-diphenylthiazole derivatives having anti-inflammatory properties are also known (Patent Application JP-01 75 475).

2-Amino-4-(4-hydroxyphenyl)thiazole derivatives which are useful as synthesis intermediates for the preparation of 2,2-diarylchromenothiazole derivatives are also known (Patent Application EP 205 069). 2-(N-methyl-N-benzylamino)thiazole derivatives are also described in J. Chem. Soc. Perkin, Trans 1, 1984, 2, 147–153 and in J. Chem. Soc. Perkin, Trans 1, 1983, 2, 341–347.

Patent Application WO 94 01423 describes 2-aminothiazole derivatives of general formula:

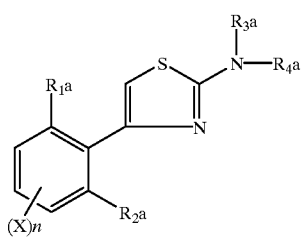

(A)

it being possible for $R_{3a}$ to represent an alkyl and $R_{4a}$ a substituted phenyl. These compounds, which are used as insecticide, have no substitution at the 5 position of the heterocycle.

Likewise, Patent Application WO 96 16650 describes compounds of general formula:

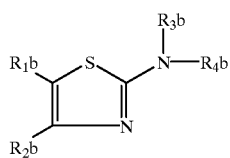

(B)

in which $R_2b$ may represent a substituted phenyl, $R_1b$ an alkyl, $R_3b$ an alkyl and $R_4b$ a sulphonyl or an acyl; these compounds are used as antibiotics.

These derivatives, whose amine at the 2 position is substituted with an unbranched pyridylalkyl radical, possess in particular a central cholinergic transmission stimulating activity. They can therefore be used as agonists of the muscarine receptors and find applications in the treatment of memory disorders and of senile dementia.

2-Aminothiazole derivatives in which the amine at the 2 position is a tertiary amine having a branched alkyl or aralkyl substituent have been described in EP 576 350 and in EP 659 747 as having affinity for the CRF receptors. None of these compounds have, as substituent of the tertiary amine at the 2 position of the thiazole ring, a substituted phenyl.

U.S. Pat. No. 5,063,245 describes antagonists of CRF which make it possible to displace in vitro the binding of CRF to its specific receptors at a concentration close to one micromole. Since then, numerous Patent Applications relating to nonpeptide molecules have been published, for example Applications WO 94/13643, WO 94/13644, WO 94/13661, WO 94/13676, WO 94/13677, WO 94/10333, WO 95/00640, WO 95/10506, WO 95/13372, WO 95/33727, WO 95/33750, WO 95/34563, EP 691 128 or EP 729 758.

It has now been found that some branched amino derivatives of thiazole, which are the subject of the present invention, exhibit excellent affinity towards the CRF receptors. Furthermore, given their structure, these molecules possess good dispersibility and/or solubility in solvents and solutions commonly used in therapy which confers pharmacological activity on them and also allow easy preparation of oral and parenteral galenic forms.

The subject of the present invention is the compounds of formula:

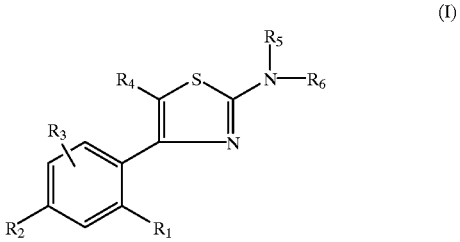

(I)

in which $R_1$ and $R_2$, which are identical or different, each represent independently a halogen atom; a $(C_1-C_5)$hydroxyalkyl; a $(C_1-C_5)$alkyl; an aralkyl in which the aryl part is a $(C_6-C_8)$ and the alkyl part is a $(C_1-C_4)$; a $(C_1-C_5)$ alkoxy; a trifluoromethyl group; a nitro group; a nitrile group; a group —SR° in which R° represents hydrogen, a $(C_1-C_5)$alkyl or an aralkyl in which the aryl part is a $(C_6-C_8)$ and the alkyl part is a $(C_1-C_4)$; a group —S—CO—R in which R represents a $(C_1-C_5)$alkyl radical or an aralkyl in which the aryl part is a $(C_6-C_8)$ and the alkyl part is a $(C_1-C_4)$; a group —COORa in which Ra represents hydrogen or a $(C_1-C_5)$alkyl; a group —CONRaRb with Ra and Rb as defined above for Ra; a group —NRaRb with Ra and Rb as defined above for Ra; a group —CONRcRd or —NRcRd in which Rc and Rd constitute, with the nitrogen atom to which they are attached, a 5- to 7-membered heterocycle; or a group —NHCO—NRaRb with Ra and Rb as defined above for Ra;

$R_3$ represents hydrogen or is as defined above for $R_1$ and $R_2$;

$R_4$ represents a $(C_1-C_5)$alkyl; a hydroxymethyl group; a formyl group; or a halogen atom;

$R_5$ represents a $(C_1-C_5)$alkyl; a cycloalkylalkyl group in which the cycloalkyl is a $(C_3-C_7)$ and the alkyl is a $(C_1-C_5)$; an alkenyl of 3 to 6 carbon atoms; a $(C_1-C_5)$ hydroxyalkyl; an alkylcarbonyloxyalkyl group in which the alkyls are a $(C_1-C_5)$; or an alkynyl group of 3 to 6 carbon atoms;

$R_6$ represents a phenyl substituted with one or more substituents Z as defined below; a monocyclic heteroaromatic $C_5-C_7$ group substituted with one or more radicals Z as defined below; or a bicyclic $C_9-C_{10}$ group consisting of an aromatic monocycle optionally comprising one or more heteroatoms selected from O, N and S, condensed with a cycloalkyl group optionally comprising in the ring one or more heteroatoms selected from O, N and S, which bicyclic group is substituted with one or more substituents Z as defined below and which is attached to the nitrogen by the ring of an aromatic nature, it being understood that $R_6$ does not represent a substituted indan and that the substituent Z represents a radical selected from: a halogen atom, a nitro group, a hydroxyl group, a trifluoromethyl group, a $(C_1-C_5)$alkyl, a $(C_1-C_5)$thioalkyl, a group —NRaRb with Ra and Rb as defined above for Ra, a $(C_1-C_5)$hydroxyalkyl, a $(C_1-C_5)$alkoxy, a trifluoromethyloxy group, an alkoxyalkyl in which the alkyls are a $(C_1-C_5)$, a group —COORa with Ra as defined above, a group —CONRaRb with Ra and Rb as defined above for Ra, a carboxy$(C_1-C_5)$alkyl, an alkoxycarbonylalkyl in which the alkyls are a $(C_1-C_5)$, a $(C_1-C_5)$ alkylcarbonyl, an alkylcarbonylalkyl in which the alkyls are a $(C_1-C_5)$, a $(C_1-C_5)$alkylcarbonyl, an alylcarbonylalkyl in which the alkyls are a $(C_1-C_5)$, a morpholinocarbonyl or morpholinocarbonyl$(C_1-C_5)$ alkyl group, or a group —NRaCOORb with Ra and Rb as defined above, a group 'NHCOR$_e$ in which $R_e$ represents a $(C_1-C_8)$alkyl, a cycloalkylcarbonyl in which the cycloalkyl is a $(C_3-C_6)$, a cycloalkylalkylcarbonyl in which the cycloalkyl is a $(C_3-C_6)$ and the alkyl a $((C_1-C_3)$, a benzoyl, a phenyl which is unsubstituted or substituted with a $(C_1-C_5)$alkyl, with a $(C_1-C_5)$alkoxy, with a halogen atom, with a nitro group, with a hydroxyl group or with a trifluoromethyl group; their stereoisomers, their addition salts, their hydrates and/or their solvates.

Monocyclic heteroaromatic group is understood to mean particularly a group selected from azepinyl, pyridyl, pyrazinyl, pyridazinyl, pyrimidyl, triazinyl, furyl and thienyl.

Examples of $(C_9-C_{10})$ bicyclic groups are 1,2,3,4-tetrahydronaphthyl as well as groups comprising one or more heteroatoms selected from N, O and S and represented, for example, by 1,2,3,4-tetrahydroquinolyl, 1,2,3,4-tetrahydroisoquinolyl, 1,2,3,4-tetrahydrophthalazinyl, 1,2,34-tetrahydroquinazolinyl, 1,2,3,4tetrahydroquinoxalinyl, 1,2,3,4tetrahydrocinnolinyl, 1,2,3,4-tetrahydrobenzotriazinyl, chromanyl, isochromanyl, indolinyl, isoindolinyl, 2,3-dihydroindazyl, 2,3-dihydrobenzoimidazolyl, 1,2-dihydrobenzotriazolyl, 2,3-dihydrobenzofuranyl, 2,3-dihydrobenzothienyl, 2,3-dihydrobenzoisothiazolyl, 2,3-dihydrobenzothiazolyl, 2,3-dihydrobenzoisoxazolyl, 2,3-dihydrobenzoxazolyl, 1,2-dihydrobenzoxazinyl, 1,2,3,4-tetrahydropteridinyl, 8,9-dihydropurinyl. These bicyclic groups are substituted with one or more substituents Z as defined above.

Examples of 5- to 7-membered heterocycles are morpholine, piperidine or pyrrolidine.

In the present description, the alkyl groups or the alkoxy groups are linear or branched.

Halogen atom is understood to mean a fluorine, chlorine, bromine or iodine atom.

Advantageous compounds according to the invention are those in which $R_6$ represents a phenyl or tetrahydronaphthyl group substituted with one or more substituents Z as defined for (I), $R_1$, $R_2$, $R_3$, $R_4$, and $R_5$ also being defined for (I), one of their stereoisomers, one of their salts, one of their hydrates and/or one of their solvates.

Among these compounds, there are particularly preferred the compounds in which $R_4$ represents a methyl, $R_1$, $R_2$, $R_5$ and $R_3$ being as defined for (I), one of their stereoisomers, one of their hydrates, and/or one of their solvates.

More particularly preferred among these compounds are those in which $R_1$ and/or $R_2$ represents a halogen, a trifluoromethyl, a $(C_1-C_5)$alkyl or a $(C_1-C_5)$alkoxy, $R_4$ represents a methyl, $R_6$ represents a phenyl at least substituted at the 2 position with a substituent Z as defined for (I), $R_3$ and $R_5$ are as defined for (I), one of theri stereoisomers, one of their salts, one of their hydrates and/or one of their solvates.

Most particularly preferred are thus the compounds:

4-(2-Chloro-4-methoxyphenyl)-5-methyl-2-[N-(5-ethoxycarbonyl-2-methoxyphenyl)-N-propylamino]thiazole 4-(2-Chloro-4-methoxyphenyl)-5-methyl-2-[N-(5-chloro-2-methylphenyl)-N-propylamino]thiazole 4-(2-Chloro-4-methoxyphenyl)-5-methyl-2-[N-(2-trifluoromethylphenyl)-N-propylamino]thiazole 4-(2-Chloro-4-methoxyphenyl)-5-methyl-2-[N-(2-methoxyphenyl)-N-propylamino]thiazole 4-(2-Chloro-4-methoxyphenyl)-5-methyl-2-[N-(2,6-dichlorophenyl)-N-propylamino]thiazole 4-(2-Chloro-4-methoxyphenyl)-5-methyl-2-[N-(2,5-dichlorophenyl)-N-propylamino]thiazole 4-(2-Chloro-4-methoxyphenyl)-5-methyl-2-[N-(2-chloro-5-methylphenyl)-N-propylamino]thiazole 4-(2-Chloro-4-methoxyphenyl)-5-methyl-2-[N-(2-chloro-5-trifluoromethylphenyl)-N-propylamino]thiazole 4-(2-Chloro-4-methoxyphenyl)-5-methyl-2-[N-(2-chloro-5-methoxyphenyl)-N-propylamino]thiazole 4-(2-Chloro-4-methoxyphenyl)-5-methyl-2-[N-(5-chloro-2-methoxyphenyl)-N-propylamino]thiazole 4-(2-Chloro-4-methoxyphenyl)-5-methyl-2-[N-(5-chloro-2-ethoxyphenyl)-N-propylamino]thiazole 4-(2-Chloro-4-methoxyphenyl)-5-methyl-2-[N-(2-methoxy-5-methylphenyl)-N-propylamino]thiazole 4-(2-Chloro-4-methoxyphenyl)-5-methyl-2-[N-(2,5-dimethylphenyl)-N-propylamino]thiazole 4-(2-Chloro-4-methoxyphenyl)-5-methyl-2-[N-(2,5-difluoromethylphenyl)-N-propylamino]thiazole 4-(2-Chloro-4-methoxyphenyl)-5-methyl-2-[N-(2-methoxy-5-trifluoromethylphenyl)-N-propylamino]thiazole 4-(2-Chloro-4-methoxyphenyl)-5-methyl-2-[N-(2,5-dimethoxyphenyl)-N-propylamino]thiazole 4-(2-Chloro-4-methoxyphenyl)-5-methyl-2-[N-(2-methoxy-5-methoxycarbonylphenyl)-N-propylamino]thiazole 4-(2,4-Dichlorophenyl-5-methyl-2-[N-(2,5dichlorophenyl)-N-propylamino]thiazole 4-(2-Chloro-4-methoxyphenyl)-5-methyl-2-[N-(5-acetyl-2-methoxyphenyl)-N-propylamino]thiazole 4-(2-Chloro-4-methoxyphenyl)-5-methyl-2-[N-(2-(methoxy)-5-(phenyl)phenyl)-N-propylamino]thiazole 4-(2-Chloro-4-methoxyphenyl)-5-methyl-2-[N-(2,6-dimethoxyphenyl)-N-propylamino]thiazole 4-(2-Chloro-4-methoxyphenyl)-5-methyl-2-[N-(2-methoxy-6-methylphenyl)-N-propylamino]thiazole 4-(2,4-Dichlorophenyl)-5-methyl-2-[N-(2-methoxy-6-methylphenyl)-N-propylamino]thiazole 4-(2-Chloro-4-methoxyphenyl)-5-methyl-2-[N-(5-ethyl-2-methoxyphenyl)-N-propylamino]thiazole 4-(2-Chloro-4-methoxyphenyl)-5-methyl-2-[N-(5-bromo-2-methoxyphenyl)-N-propylamino]thiazole 4-(2-Chloro-4-methoxyphenyl)-5-methyl-2-[N-(2-methoxy-5-o-tolylphenyl)-N-propylamino]thiazole 4-(2,4,6-Trichlorophenyl)-5-methyl-2-[N-(2,5-ditrifluoromethylphenyl)-N-propylamino]thiazole 4-(2,4-Dichlorophenyl)-5-methyl-2-[N-(2,5-ditrifluoromethylphenyl)-N-propylamino]thiazole 4-(2-Chloro-4-methoxyphenyl)-5-methyl-2-[N-(2-methoxy-5-nitrophenyl)-N-propylamino]thiazole 4-(2,4-Dichlorophenyl)-5-methyl-2-[N-(2,6-dichloro-5-methylphenyl)-N-propylamino]thiazole 4-(2,4-Dichlorophenyl)-5-methyl-2-[N-(2-methoxy-6-methylphenyl)-N-propylamino]thiazole 4-(2,4-Dichlorophenyl)-5-methyl-2-[N-(5-chloro-2-methylphenyl)-N-propylamino]thiazole 4-(4-Chloro-2-trifluoromethylphenyl)-5-methyl-2-[N-(5-chloro-2-methylphenyl)-N-propylamino]thiazole 4-(2-Chloro-4-methoxy-5-methylphenyl)-5-methyl-2-[N-(2-methoxy-5-methylphenyl)-N-propylamino]thiazole 4-(2-Chloro-4-methoxyphenyl)-5-methyl-2-[N-(2-methylthio-5-trifluoromethylphenyl)-N-propylamino]thiazole 4-(2,4-Dichloro-5-methylphenyl)-5-methyl-2-[N-(2-methoxy-5-methylphenyl)-N-propylamino]thiazole 4-(2-Chloro-4,5-dimethylphenyl)-5-methyl-2-[N-(2-methoxy-5-methylphenyl)-N-propylamino]thiazole 4-(2-Chloro-4-methoxyphenyl)-5-methyl-2-[N-(2-methoxy-5-methoxycarbonylphenyl)-N-propylamino]thiazole 4-(2-Chloro-4,5-methoxyphenyl)-5-methyl-2-[N-(5-chloro-2-methylphenyl)-N-prop-2-ynylamino]thiazole one of their stereoisomers, one of their salts, one of their hydrates and/or one of their solvates.

The compounds of the invention in free form generally exhibit basic properties. However, depending on the nature of the substituents, some may exhibit acidic properties.

The salts of the compounds of formula (I) with pharmaceutically acceptable acids or bases (when this is possible) are the preferred salts, but those which make it possible to isolate the compounds of formula (I), in particular to purify them or to obtain pure isomers also form the subject of the invention.

Among the pharmaceutically acceptable acids for the preparation of the addition salts of the compounds of formula (I), there may be mentioned hydrochloric, phosphoric, fumaric, citric, oxalic, sulphuric, ascorbic, tartaric, maleic, mandelic, methanesulphonic, lactobionic, gluconic, glucaric, succinic, sulphonic and hydroxypropanesulphonic acids.

Among the pharmaceutically acceptable bases for the preparation of the addition salts with the compounds of formula (I) when these have acidic properties, there may be mentioned sodium, potassium or ammonium hydroxide.

The compounds according to the invention as well as the intermediate useful for their preparation are prepared according to methods well known to persons skilled in the art, in particular according to EP 576 350 and EP 659 747.

The following reaction scheme illustrates a process of preparation for the synthesis of the compounds (I).

SCHEME 1

 

 

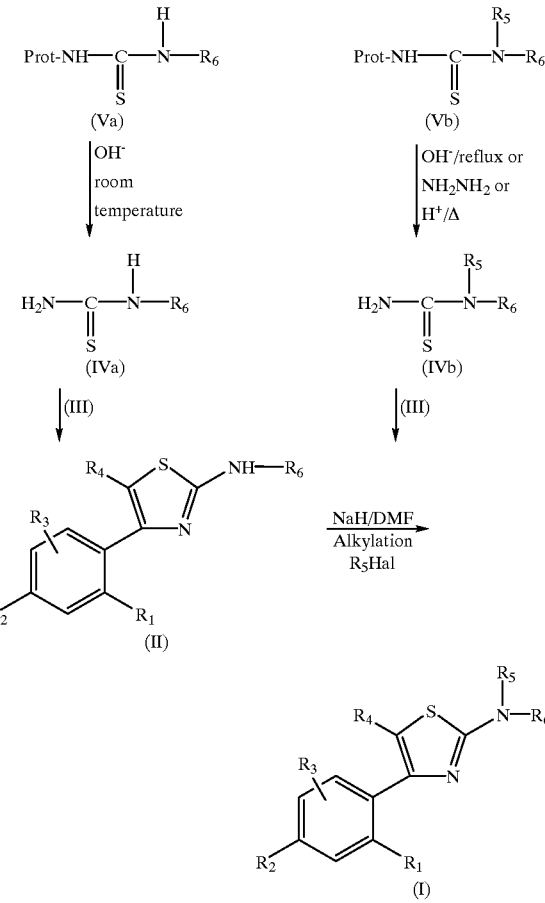

According to another of its features, the subject of the present invention is also a process for the preparation of the compounds of formula (I), characterized in that an alpha-halogenated, preferably alpha-brominated or alpha-chlorinated, derivative of formula (III)

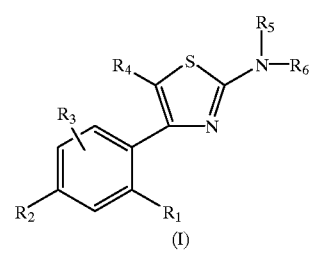

in which $R_1$, $R_2$, $R_3$ and $R_4$ are as defined for (I) and Hal represents a halogen, preferably bromine or chlorine, atom, is reacted either with a thiourea (ROUTE A) of formula:

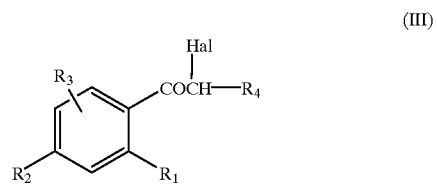

in which $R_6$ is as defined for (I) in order to obtain a compound of formula (II)

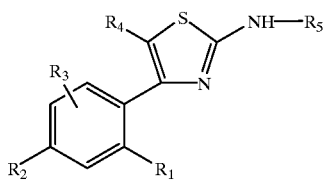
(II)

in which $R_1$, $R_2$, $R_3$, $R_4$ and $R_6$ are as defined for (I) in order to then subject it to an alkylation reaction in order to provide the compound (I), or with a thiourea (ROUTE B) of formula

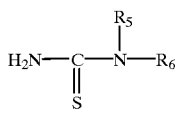
(IVb)

in which $R_5$ and $R_6$ are as defined for (I) in order to give directly the compound (I), and, where appropriate, the compounds of formula (I) thus obtained are then optionally separated into their possible stereoisomers and/or salified in order to form the corresponding salts.

The alkylation reactions used in the above process are carried out under the usual conditions known to persons skilled in the art by the action of an appropriate alkylating agent such as, for example, an alkyl halide in the presence of a base, preferably sodium hydride.

The derivatives of formula (III) can be obtained from the corresponding nonhalogenated ketones of formula

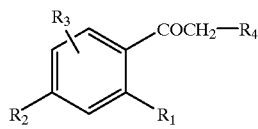

in which $R_1$, $R_2$, $R_3$ and $R_4$ are as defined for (I) either (i) by the action of bromine in an appropriate organic solvent, such as acetic acid, carbon tetrachloride or diethyl ether, or (ii) by the action of quaternary ammonium tribromides according to the method described in Bull. Chem. Soc. Japan, 1987, 60, 1159–1160 and 2667–2668, or (iii) alternatively by the action of copper(II) bromide in an organic solvent, such as a mixture of chloroform and ethyl acetate according to J. Org. Chem. 1964, 29, 3451–3461. As a variant, the compounds of formula (II) can be obtained by the action of 2-bromopropionyl bromide on a substituted benzene of formula

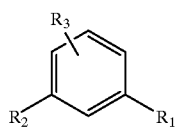

by a Friedel-Crafts reaction.

The abovementioned ketones are in general known or commercially available products. These compounds can be prepared by Friedel-Crafts reaction, in the presence of a Lewis acid according to methods well known to persons skilled in the art.

The thiourea derivatives (IVa) and (IVb) are obtained from the compounds

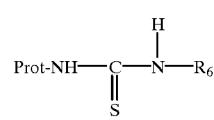
(Va)

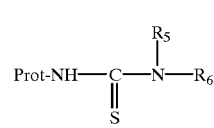
(Vb)

in which Prot represents a protecting group, for example benzoyl or pivaloyl, $R_5$ and $R_6$ being as defined above for (I), either by a basic treatment, preferably using ammonia, sodium hydroxide or hydrazine at a temperature ranging from room temperature to the reflux temperature of the reaction mixture, or by an acidic treatment preferably using hydrochloric acid.

The compounds of formula (Va) and (Vb) are prepared by reacting, according to known methods, an isothiocyanate, for example a benzoyl isothiocyanate or a pivaloyl isothiocyanate, with the corresponding amines of formula (VIa) and (VIb)

(VIa)

(VIb)

in which $R_5$ and $R_6$ are as defined for (I).

The secondary amines (VIb) are prepared from primary amines $$R_6-NH_2 \quad (VIa)$$

either by reacting with an aldehyde of formula $R'_5$—CHO in which $R'_5$ represents $R_5$ as defined for (I) shortened by one carbon atom in the linear alkyl part, then reducing the imine with an alkali metal hydride, for example with $NaBH_4$, in an alkanol, preferably in ethanol or methanol, at room temperature, or by reacting with an acid of formula $R'_5COOH$ which serves both as reagent and as solvent, the aldehyde being formed in situ during the addition of the alkali metal hydride, or by reacting with an acid halide or an acid anhydride in an organic solvent selected from the halogenated hydrocarbons, such as dichloromethane, in the presence of a proton acceptor, preferably triethylamine. The amide derived from this reaction is then reduced with an alkali metal hydride such as $AlLiH_4$ in organic solvents of the diethyl ether type.

The compounds of formula (I) above also comprise those in which one or more hydrogen or carbon atoms have been replaced by their radioactive isotope, for example tritium or carbon-14. Such labelled compounds are useful in research, metabolism or pharmacokinetic work, or alternatively in biochemical tests as receptor ligands.

The compounds of the present invention have been the subject of biochemical and pharmacological studies. They possess highly advantageous pharmacological properties. The compounds of the invention displace, at concentrations less than 10 μm, the binding of CRF or of iodinated related peptides (urotensin, sauvagin) to the specific receptors present on the membranes of animal (rats, mice) or human brains and on cultured cells, according to the method described by E. B. De Souza (J. Neurosci., 1987, 7, 1, 88–100).

This is surprising and unexpected since compounds of similar structure to that of the compounds of the invention do not significantly displace this binding. CRF is a neuropeptide which controls the activity of the hypothalamo-hypophysoadrenal axis. This factor is responsible for stress-related endocrine and behavioural responses.

Indeed, it has been demonstrated that CRF can modulate behaviour like also certain functions of the autonomous nervous system (G. F. Koob, F. E. Bloom, Fed. Proc., 1985, 44, 259; M. R. Brown, L. A. Fisher, Fed. Proc., 1985, 44, 243). More particularly, CRF induces the secretion of corticotropin (ACTH), β-endorphins and other peptides derived from proopiomelanocortin (A. Tazi et al., Regul. Peptides, 1987, 18, 37; M. R. Brown et al., Regul. Peptides, 1986, 16, 321; C. L. Williams et al., Am. J. Physiol., 1987, G 582, 253).

The compounds of the invention may therefore be useful for the regulation of the secretion of these endogenous substances. They find more especially applications as active ingredients of medicaments for reducing the response to stress (behaviour, emotional states, gastrointestinal and cardiovascular disorders, immune system disorders) and more generally in pathologies involving CRF, for example psychiatric disorders, anxiety, depression, nervous anorexia, sexual activity and fertility disorders, Alzheimer's disease and the like.

The compounds of the invention are very stable and are therefore thereby particularly appropriate for constituting the active ingredient of medicaments.

The invention also extends to the pharmaceutical compositions containing, as active ingredient, a compound of formula (I) or one of its pharmaceutically acceptable salts, optionally in combination with one or more inert and appropriate excipients.

In each dosage unit, the active ingredient of formula (I) is present in quantities suited to the daily doses envisaged. Each dosage unit is suitably adjusted according to the dosage and the type of administration expected, for example tablets, gelatine capsules and the like, sachets, ampoules, syrups and the like, drops, transdermal or transmucosal patch, such that such a dosage unit contains 0.5 to 200 mg of active ingredient, preferably 0.5 to 800 mg which should be administered daily.

The compounds of the invention can also be used in combination with another active ingredient useful for the desired therapy, such as for example anxiolytics, antidepressants or anorexigenic agents.

The compounds of formula (I) are not very toxic; their toxicity is compatible with their use as a medicament for the treatment of the above disorders and diseases.

The compounds of formula (I) can be formulated in pharmaceutical compositions for administration to mammals, including humans, for the treatment of the above-mentioned diseases.

The pharmaceutical compositions thus obtained are advantageously provided in various forms, such as for example injectable or oral solutions, sugar-coated tablets, plain tablets or gelatine capsules. The pharmaceutical compositions containing, as active ingredient, at least one compound of formula (I) or one of its salts, are in particular useful for the treatment, for preventive or curative purposes, of stress-related diseases and more generally in the treatment of any pathology involving CRF, such as for example: Cushing's disease, neuropsychiatric disorders such as depression, anxiety, panic, obsessive-compulsive disorders, mood disorders, behavioural disorders, aggressiveness, anorexia, bulimia, hyperglycaemia, retarded growth, sleep disorders, epilepsy and depressions of all types; Alzheimer's disease, Parkinson's disease; Huntingdon's chorea; amyotrophic lateral sclerosis; vascular, cardiac and cerebral disorders; sexual activity and fertility disorders; immunodepression, immunosuppression, inflammatory processes, multiple infections, rheumatoid arthritis, osteoarthritis, uveitis, psoriasis as well as diabetes; cancers, gastrointestinal disorders and inflammations resulting therefrom (irritable and inflammatory colon, diarrhoea); disorders in the perception of pain, fibromyalgias related or otherwise to sleep disorders, fatigue, migraine; symptoms related to (alcohol) dependency and to drug withdrawal.

The dosage can vary widely according to the patient's age, weight and state of health, the nature and seriousness of the condition, as well as the route of administration. This dosage comprises the administration of one or more doses of about 0.5 mg to 200 mg per day, preferably of about 0.5 to 800 mg per day.

In the pharmaceutical compositions of the present invention for oral, sublingual, subcutaneous, intramuscular, intravenous, transdermal, transmucosal, local or rectal administration, the active ingredient may be administered in unit forms for administration, mixed with conventional pharmaceutical carriers, to animals and to human beings. The appropriate unit forms for administration comprise the oral forms such as tablets, gelatine capsules, powders, granules and oral solutions or suspensions, forms for sublingual and oral administration, forms for subcutaneous, intramuscular, intravenous, intranasal or intraocular administration and forms for rectal administration.

When a solid composition in the form of tablets is prepared, the principal active ingredient is mixed with a pharmaceutical vehicle such as gelatin, starch, lactose, magnesium stearate, talc, gum arabic and the like. The tablets can be coated with sucrose or other appropriate materials or alternatively they can be treated so that they have a prolonged or delayed activity and so that they continuously liberate a predetermined quantity of active ingredient.

A preparatin in gelatine capsules is obtained by mixing the active ingredient with a diluent and by pouring the mixture obtained into soft or hard gelatine capsules.

A preparation in syrup or elixir form may contain the active ingredient together with a sweetener, preferably calorie free, methylparaben and propylparaben as antiseptic, as well as a taste-enhancing agent and an appropriate colouring.

The water-dispersible powders or granules may contain the active ingredient in the form of a mixture with dispersing agents or wetting agents, or suspending agents, such as polyvinylpyrrolidone, as well as with sweeteners or flavour correctors.

For rectal administration, suppositories are used which are prepared with binders which melt at the rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersing agents and/or wetting agents, for example propylene glycol or butylene glycol.

For transmucosal administration, the active ingredient may be formulated in the presence of an enhancer such as a bile salt, a hydrophilic polymer such as for example hydroxypropyl cellulose, hydroxypropyl methylcellulose, hydroxyethyl cellulose, ethyl cellulose, carboxymethylcellulose, dextran, polyvinylpyrrolidone, pectins, starches, gelatin, casein, acrylic acids, acrylic esters and copolymers thereof, vinyl polymers or copolymers, vinyl alcohols, alkoxy polymers, polymers of polyethylene oxide, polyethers or mixtures thereof.

The active ingredient can also be formulated in the form of microcapsules, optionally with one or more carriers or additives.

The active ingredient may also be provided in the form of a complex with a cyclodextrin, for example α-, β- or γ-cyclodextrin, 2-hydroxypropyl-β-cyclodextrin or methyl-β-cyclodextrin.

The following EXAMPLES, given with no limitation being implied, illustrate the invention.

In the PREPARATIONS, there are described the methods of synthesis of the various intermediates which make it possible to obtain the compounds of the invention. These intermediates are all obtained according to methods well known to persons skilled in the art.

The melting points were measured according to the Micro-Köfler technique are expressed in degrees Celsius.

The proton nuclear magnetic resonance spectra ($^1$H NMR) of the compounds of formula (I) were recorded, depending on the case, at 200 MHz or at 100 MHz. The chemical shifts are given in ppm and the coupling constants in Hertz.

The compounds of the invention exhibit a percentage analysis in accordance with theory.

The compounds of the invention which are described in TABLE I also have NMR spectra in accordance with their structure.

PREPARATIONS

PREPARATION OF THE KETONES OF FORMULA III

PREPARATION I
2-Bromo-1-(2,4-dichlorophenyl)propan-1-one (Compound 1-1)

17.4 g of tetrabutylammonium tribromide are added to 7 g of 1-(2,4-dichlorophenyl)propan-1-one in solution in a mixture of 420 ml of dichloromethane and 140 ml of methanol, at room temperature. After 24 hours, the reaction mixture is concentrated under vacuum. The residue is taken up in water, extracted with ethyl acetate and the organic phase is dried with sodium sulphate and evaporated under vacuum; then the residue is purified on a silica gel column with, as eluent, a cyclohexane/ethyl acetate 20/1 (v/v) mixture in order to obtain an oil.

In the same manner, there may be obtained, using the appropriate ketones, the following compound: 2-bromo-1-(2-chloro-4-methoxyphenyl)propan-1-one (Compound 1-2)

PREPARATION II
2-Bromo-1-(2-chloro-4-trifluoromethylphenyl)propan-1-one (Compound 2-1)

Stage 1: At 0° C., under an inert atmosphere, 63 ml of a solution (3M) of ethylmagnesium in diethyl ether are added to a solution of 19.5 g of 3-chloro-4-cyanobenzotrifluoride in 250 ml of ether. After reacting for 4 hours at room temperature, the reaction mixture is again cooled to 0° C. 5 ml of hydrochloric acid (10 N) are added. When the addition is complete, the mixture is heated under reflux (60° C.) for 1 hour. After returning to room temperature, the aqueous phase is extracted with ether and then with dichloromethane. The organic phases are washed with a saturated NaCl solution before being dried over sodium sulphate. After evaporation under vacuum, the residue is purified on a silica gel; eluent cyclohexane/ethyl acetate 20/1 (v/v); yield=92%.

$^1$H NMR (DMSO): 1.10(t,3H); 2.94(q,2H); 7.84(s,2H); 7.92(s,1H).

Stage 2: At room temperature, 26 g of tetrabutylammonium tribromide are added to 11.8 g of the product obtained above in solution in 500 ml of dichloromethane. The mixture is then heated for 3 hours at 35–40° C. Again at room temperature, the organic phase is washed with water and then with a saturated NaCl solution before drying it over sodium sulphate. It is evaporated under vacuum; yield=97%.

$^1$H NMR (CDCl$_3$): 0.89(d,3H); 5.16(q,1H); 7.61(m,2H); 7.67(m,1H).

PREPARATION III
2-Bromo-1-(2,4,6-trichlorophenyl)ethan-1-one (Compound 3-1)

At 0° C., under argon, to a solution of 31.1 g of 1,3,5-trichlorobenzene, there are added 15.2 ml of bromoacetyl bromide, followed by 23.3 g of aluminium chloride in small portions (over 2 hours). The reaction mixture is then heated for 8 hours at 80° C. After returning to room temperature, it is diluted with dichloromethane and then hydrochloric acid (1 N) is added at 0° C. The aqueous phase is extracted with dichloromethane, the organic phases are combined, washed with water and then dried over sodium sulphate. The evaporation residue is purified on silica: yield=70%.

$^1$H NMR (DMSO): 4.77(s,2H); 7.85(s,2H).

A variant of this process consists in using a CH$_2$Cl$_2$ solvent and in operating at a temperature close to 10° C. Starting with 1.3-dichloro-4-methylbenzene, 2-bromo-1-(2,4-dichloro-5-methylphenyl)ethan-1-one (Compound 3-2) is obtained.

2-Bromo-1-(2-chloro-4,5-dimethylphenyl)ethan-1-one (Compound 3-3) is prepared in the same manner.

PREPARATION OF THE AMINES

PREPARATION IV
6-Amino-7-methoxy-1,2,3,4-tetrahydronaphthalene (Compound 4-1)

Stage 1: 12.0 ml of 7-methoxy-1,2,3,4-tetrahydronaphthalene are dissolved in 100 ml of acetic anhydride and then 3.6 ml of fuming nitric acid, dissolved in 10 ml of acetic anhydride, are added. The reaction mixture is stirred for one hour at room temperature.

After ice has been added, the mixture is neutralized with 10 N sodium hydroxide and extracted with ethyl acetate. The resulting solution is dried over sodium sulphate and then evaporated to dryness. The residue obtained is purified by chromatography on a silica gel column eluted with an ethyl acetate/hexane 10/90 (v/v) mixture for the separation of the two isomers. 3.3 g of the expected product are obtained in the form of yellow crystals.

Stage 2: 3.2 g of the product obtained above are dissolved in 60 ml of acetic acid and 30 ml of concentrated hydrochloric acid and then 10 g of SnCl$_2$.H$_2$O are added and the reaction mixture is heated under reflux for 3 hours. It is evaporated and then the residue obtained is taken up in a saturated sodium carbonate solution and extracted with ethyl acetate. The resulting solution is dried over sodium sulphate and then evaporated to dryness. 2.65 g of the expected product are obtained in the form of crystals; yield=97%.

$^1$H NMR (CDCl$_3$):1.74–1.80(m,4H, —CH$_2$—CH$_2$—); 2.64–2.68(m,4H, —CH$_2$—CH$_2$—CH$_2$—CH$_2$); 3.67(m,2H, —NH$_2$); 3.68(s,3H, —OCH$_3$); 6.46(s,1H,H$_1$); 6.51(s,1H, H$_4$).

PREPARATION V
N-Propyl-2,4-dichloroaniline (Compound 5-1)

Stage 1: To a solution of 9.2 g of 2,4-dichloroaniline in 100 ml of anhydrous methylene chloride, there are added, under argon at 0° C., 9.5 ml of triethylamine followed, dropwise, by 5.9 ml of propionyl chloride. The temperature of the reaction mixture is then allowed to rise to room temperature. The organic phase is washed with water and then with a saturated NaCl solution, it is dried over sodium sulphate and evaporated to dryness under vacuum. After solubilization of the residue obtained in dichloromethane with the use of heat, isopropyl ether is added.

9.6 g of the desired product are obtained in the form of white crystals; yield=80%; m.p.=121° C.

Stage 2: 50 ml of a 1 M solution of lithium aluminium hydride in tetrahydrofuran are added slowly and under argon to 9.6 g of the product previously obtained in solution in 80 ml of tetrahydrofuran. The reaction mixture is heated under reflux for 2 hours. At 0° C., the excess lithium aluminium hydride is carefully destroyed by addition of water and then of sodium hydroxide. After removing the precipitate, the organic solution is evaporated to dryness under vacuum. The residue obtained is taken up in diethyl ether and then extracted with a 1 N solution of hydrochloric acid. The aqueous phase is adjusted to pH=12 and extracted with dichloromethane. The organic phase is dried over sodium sulphate and then evaporated off. 7.5 g of the expected product are obtained in the form of an oil; yield=84%.

$^1$H NMR (CDCl$_3$): 0.99(t,2H); 1.57(m,2H); 3.01(t,2H); 4.27(1H); 6.4–7.2(m,3H).

By carrying out the procedure as indicated for PREPARATION V above, and by using, as raw maerials, the appropriate primary amines, the following are prepared:
N-Propyl-2-chloroaniline (Compound 5-2)
N-Propyl-3-chloroaniline (Compound 5-3)
N-Propyl-2-methylaniline (Compound 5-4)
N-Propyl-2-methoxyaniline (Compound 5-5)
N-Propyl-2-trifluoromethoxyaniline (Compound 5-6)
N-Propyl-2,6-dichloroaniline (Compound 5-7)
N-Propyl-2,5-dichloroaniline (Compound 5-8)
N-Propyl-2-chloro-5-trifluoromethylaniline (Compound 5-9)
N-Propyl-2-chloro-5-methoxyaniline (Compound 5-10)
N-Propyl-5-chloro-2-methoxyaniline (Compound 5-11)
N-Propyl-5-chloro-2-ethoxyaniline (Compound 5-12)
N-Propyl-2,5-dimethylaniline (Compound 5-13)
N-Propyl-2-methoxy-5-methylaniline (Compound 5-14)
N-Propyl-2-methoxy-5-trifluoromethylaniline (Compound 5-15)
N-Propyl-2,5-dimethoxyaniline (Compound 5-16)
N-Propyl-2,4,6-trichloroaniline (Compound 5-17)
N-Propyl-2,6-dimethoxyaniline (Compound 5-18)

PREPARATION VI
N-Propyl-5-bromo-2-methoxyaniline (Compound 6-1)

Stage 1: by carrying out the procedure according to Simada T. (Sci. Pap. Inst. Phys. Chem. Res. Jpn., Vol. 35, No. 884, pp 365–371, 1938), 5-bromo-2-methoxynitrobenzene is obtained from 4-bromo-2-nitrophenol.

$^1$;H NMR (CDCl$_3$): 3.94(s,3H); 7.06(d,1H); 7.64(dd,1H); 8.23(d,1H).

Stage 2: the product obtained above is reduced in the presence of iron and concentrated hydrochloric acid in an ethanol-water mixture. The 5-bromo-2-methoxyaniline obtained undergoes acylation followed by reduction as described in PREPARATION V.

$^1$H NMR (CDCl$_3$): 1.00(t,3H); 1.66(m,2H); 3.05(t,2H); 3.81(s,3H); 4.25(m,1H); 6.55–6.74(m,3H).

PREPARATION VII
N-Propyl-2-methoxy-6-methylaniline (Compound 7-1)

Stage 1: Starting with 2-methoxy-6-methylaniline, N-propionyl-2-methoxy-6-methylaniline is obtained by following the procedure described above (PREPARATION V, Stage 1).

$^1$H NMR (CDCl$_3$): 1.29(t,3H); 2.21(s,3H); 2.48(q,2H); 3.78(s,3H); 6.70–6.83(m,3H); 7.06–7.14(m,1H).

Stage 2: at 0° C. under argon, 11.9 g of sodium borohydride (3.5 equivalents) are added to 180 ml of a 1 M solution of titanium tetrachloride (2 equivalents). The solution of 19 g of N-propionyl-2-methoxy-6-methylaniline in 100 ml of dimethoxyethane is added slowly to the reaction mixture so that the temperature of the mixture is between 5 and 15° C. When the addition is complete, the mixture is heated to around 65° C. At 0° C., the mixture is then hydrolyzed very slowly and then alkalinized with the aid of sodium hydroxide. The aqueous phase is extracted with dichloromethane.

The organic phases are washed with water and then with a saturated NaCl solution before being dried over sodium sulphate and evaporated under vacuum; yield=58%.

$^1$H NMR (CDCl$_3$): 0.95(t,3H); 1.57(m,2H); 2.27(s,3H); 3.00(t,2H); 3.77(s,3H); 6.65–6.80(m,3H).

PREPARATION VIII
N-Propyl-2methoxy-5-methoxycarbonylaniline (Compound 8-1)

15 g of 2-methoxy-5-methoxycarbonylaniline are dissolved in 500 ml of propionic acid under argon and at room temperature and 15.7 g of sodium borohydride are added in small portions. The reaction mixture is stirred for 2 hours and then hydrolyzed and alkalinized with 10 N sodium hydroxide while the temperature is maintained below 20° C. It is extracted with dichloromethane, the organic phase is washed with a saturated NaCl solution, dried and then evaporated under vacuum. The expected product is obtained in the form of an oil with a quantitative yield.

By carrying out the procedure as described for PREPARATION VIII above, and using the appropriate primary amine, the following are prepared:
N-Propyl-2,5-ditrifluoromethylaniline (Compound 8-2)
N-Propyl-2-chloro-5-methylaniline (Compound 8-3)
N-Propyl-2-methoxy-5-phenylaniline (Compound 8-4)
N-Propyl-5-ethyl-2-methoxyaniline (Compound 8-5)
N-Propyl-5-chloro-2,4-dimethoxyaniline (Compound 8-6)
N-Propyl-4-chloro-2,5-dimethoxyaniline (Compound 8-7)
N-Propyl-2-chloro-5-methoxy-4-methoxycarbonylaniline (Compound 8-8)
N-Propyl-2-thiomethyl-5-trifluoromethylaniline (Compound 8-9)
N-Propyl-2-methyl-5-methoxycarbonylaniline (Compound 8-10)

PREPARATION OF THE THIOUREAS
PREPARATION IX
N-(7-Methoxy-1,2,3,4-tetrahydronaphth-6-yl)thiourea (Compound 9-1)

1.45 g of ammonium thiocyanate are dissolved in 30 ml of acetone and after 2.2 ml of benzoyl chloride have been added, the reaction mixture is heated under reflux for 15 minutes. 2.6 g of 6-amino-7-methoxy-1,2,3,4-tetrahydronaphthalene (Compound 4-1) dissolved in 20 ml of acetone are added and then the mixture is heated under reflux for 30 minutes. It is evaporated to dryness, the residue obtained is taken up in a minimum of ethanol, 50 ml of 30% ammonium hydroxide are added and the mixture is heated under reflux for 20 hours. The thiourea obtained is cooled, filtered, washed with waer and then with an ethyl acetate/ hexane 25/75 (v/v) mixture. 2.8 g of the expected product are obtained in the form of a beige powder; yield=80%.

PREPARATION X

N-(2,4-Dichlorophenyl)-N-propylthiourea (Compound 10-1)

Stage 1: 5.1 ml of benzoyl chloride are added under argon and at 0° C. to 3.4 g of ammonium thiocyanate in 80 ml of anhydrous acetone and the reaction mixture is stirred for 15 minutes. 7.48 g of N-propyl-2,4-dichloroaniline (Compound 5-1) in 60 ml of anhydrous acetone are added and the reaction mixture is stirred for 2 hours at room temperature. It is evaporated to dryness, the residue obtained is taken up in dichloromethane, washed with water and dried. 13.5 g of the expected product are obtained in the form of an oil; yield=82%.

Stage 2: 3.6 ml of hydrazine are added to 13.5 g of the product previously obtained in solution in 150 ml of methanol. The reaction mixture is left for 12 hours at room temperature. The methanol is evaporated off, the residue obtained is taken up in dichloromethane and then the mixture is washed with water and evaporated to dryness. The residue is purified by chromatography on a silica gel column eluted with an ethyl acetate/cyclohexane 1/3 (v/v) mixture. 6.9 g of the expected product are obtained in the form of crystals; yield=71%; m.p.=121° C.

By carrying out the procedure as indicated for Stage 1 of PREPARATION X above, and by using N-propyl-2-methoxy-5-methoxycarbonylaniline (Compound 8-1), N'-benzoyl-N-(2-methoxy-5-methoxycarbonylphenyl)-N-propylthiourea (Compound 10-2) is prepared.

PREPARATION XI

N-(5-Chloro-2-methylphenyl)thiourea (Compound 11-1)

Stage 1: 8.9 ml of benzoyl chloride are added to a solution of 5.9 g of ammonium thiocyanate in 130 ml of anhydrous acetone. The reaction mixture is heated under reflux for 15 minutes and then after cooling, 10 g of 5-chloro-2-methylaniline are added. The reaction mixture is heated under reflux for 2 hours and the acetone is removed by distillation under vacuum. The residue obtained is taken up in dichloromethane. The mixture is washed with water, dried over sodium sulphate and evaporated under vacuum. The expected product is obtained in the form of an oil with a quantitative yield.

Stage 2: The product obtained above is heated at 90° C. for 16 hours in the presence of 300 ml of a 5% sodium hydroxide solution. After cooling, the reaction mixture is adjusted to pH=7 by addition of a 1 N solution of hydrochloric acid. The product precipitates and 10.53 g of the expected product are obtained in the form of yellow crystals: yield=74%; m.p.=137° C.

PREPARATION XII

N-(5-Carboxy-2-methoxyphenyl)-N-propylthiourea (Compound 12-1)

The expected product is obtained from N'-benzoyl-N-(2-methoxy-5-methoxycarbonylphenyl)-N-propylthiourea (Compound 10-2) by carrying out the procedure according to PREPARATION X and by using an excess of sodium hydroxide to obtain, in addition to the deprotection of the thiourea, the saponification of the ester.

By carrying out the procedure according to PREPARATIONS I to XII above, the intermediates allowing the synthesis of the compounds (I) according to the invention are prepared using the appropriate starting materials.

EXAMPLE 1

4-(2-Chloro-4-methoxyphenyl)-5-methyl-2-[N-(7-methoxy-1,2,3,4-tetrahydronaphth-6-yl)-N-propylamino]thiazole hydrochloride (I) $R_1$=Cl; $R_2$=OCH$_3$; $R_3$=H; $R_4$=CH$_3$; $R_5$=—CH$_2$CH$_2$Ch$_3$ $R_6$ = 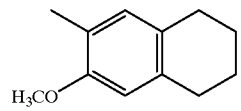

Stage 1: 1.4 g of 2-bromo-1-(2-chloro-4-methoxyphenyl)-propan-1-one (Compound 1-2) are dissolved in 50 ml of methanol and then 1.3 g of N-(7-methoxy-1,2,3,4-tetrahydronaphth-6-yl)thiourea (Compound 9-1) are added. The reaction mixture is heated under reflux for 12 hours, it is evaporated to dryness and then the residue obtained is taken up in a saturated sodium carbonate solution. The resulting solution is extracted with ethyl acetate, dried over sodium sulphate and evaporated to dryness. The residue is purified by chromatography on a silica gel column eluted with an ethyl acetate/hexane 25/75 (v/v) mixture. The precipitate obtained is taken up in petroleum ether and then filtered.

1.3 g of the expected product are obtained in the form of a white powder (yield=62%).

$^1$H NMR (CDCl$_3$): 1.78–1.82(m,4H, —CH$_2$—CH$_2$);2.24 (s,3H, —CH$_3$); 2.73–2.75(m,4H, —CH$_2$—CH$_2$—); 3.85(s, 3H, OCH$_3$); 3.86(s,3H, —OCH$_3$); 6.58(s,1H, H$_4$); 6.87(dd, J=2.5,J=8.4 1H, H$_5$); 7.02(d,J=2.5,1H,H$_3$); 7.35(d,J=8.7,1H, H$_6$), 7.46(s,1H, H$_6$); 7.46(s,1H,H$_1$); 7.47(s,1H, —NH—).

Stage 2: 1.0 g of the product previously obtained, dissolved in 20 ml of anhydrous dimethylformamide, is added to a suspension of 0.17 g of sodium hydride in 20 ml of dimethylformamide. 0.44 ml of bromopropane is added and then the reaction mixture is stirred at room temperature for one hour. 100 ml of a saturated ammonium chloride solution are then added, the mixture extracted with ethyl acetate and then the organic phase washed with a saturated NaCl solution.

It is dried over sodium sulphate and evaporated to dryness. The residue is purified by chromatography on a silica gel column eluted with an ethyl acetate/hexane 10/90 (v/v) mixture. 0.89 g of the expected product is isolated in the form of a colourless oil. The hydrochloride is obtained by adding to the product, previously dissolved in diethyl ether, petroleum ether followed by diethyl ether saturated with gaseous hydrochloric acid until total precipitation of the salt is obtaine; m.p.=101° C.

$^1$H NMR (CDCl$_3$): 0.85(t,J=7.3, 3H, —CH$_2$—CH$_3$); 1.46–1.57(m,2H, —CH$_2$—CH$_3$); 1.72(m,4H, —CH$_2$—CH$_2$—); 1.99(s,3H, —CH$_3$); 2.65–2.77 (m,4H, —CH$_2$—CH$_2$—); 3.73–3.83(m, with at 3.78(s,3H, —OCH$_3$) and at 3.83(s,3H, —OCH$_3$); 2H, —N—CH$_2$—CH$_2$); 6.96(s,1H, H$_1$); 7.04(dd,J=2.5,J=8.4, 1H, H$_5$); 7.15(s,1H,H$_1$); 7.20(d, J=2.5,H$_3$); 7.43(d,J=8.4,1H,H$_6$).

EXAMPLE 2

4-(2,4-Dichlorophenyl)-5-methyl-2[N-(2,4-dichlorophenyl)-N-propylamino]thiazole (I): $R_1$=Cl; $R_2$=Cl; $R_3$=H; $R_4$=CH$_3$; $R_5$=—CH$_2$CH$_2$CH$_3$ $R_6$ =

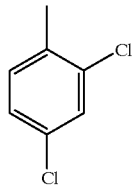

To 1.07 g of N-(2,4-dichlorophenyl)-N-propylthiourea (Compound 10-1) in 6 ml of ethanol, there is added 1 ml of triethylamine followed, dropwise, by 1.3 g of 2-bromo-1-(2,4-dichlorophenyl)propan-1-one (Compound 1-1). The reaction mixture is heated for 3 hours at 78° C., it is evaporated to dryness and then the residue is taken up in dichloromethane. The organic phase is washed with water, dried over sodium sulphate and evaporated to dryness under vacuum.

The residue is purified by chromatography on a silica gel column eluted with a cyclohexane/ethyl acetate 3/1 (v/v) mixture. 1.31 g of the expected product are obtained in the form of crystals in pentane; yield=72%; m.p.=90° C.

EXAMPLE 3

4-(2-Chloro-4-methoxyphenyl)-5-methyl-2-[N-(5-carboxy-2-methoxyphenyl)-N-propylamino]thiazole (I): $R_1$=Cl; $R_2$=OCH$_3$; $R_3$=H; $R_4$=CH$_3$; $R_5$=—CH$_2$CH$_2$CH$_3$;

$R_6$ =

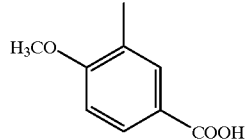

By following the procedure of EXAMPLE 2 and by using 2-bromo-1-(2-chloro-4-methoxyphenyl)propan-1-one (Compound 1-2) and N-(2-methoxy-5-carboxyphenyl)-N-propylthiourea (Compound 12-1), the expected product is obtained in the form of white crystals; yield=70%; m.p.=109° C.

EXAMPLE 4

4-(2-Chloro-4-methoxyphenyl)-5-methyl-2-[N-(5-ethoxycarbonyl-2-methoxyphenyl)-N-propylamino]thiazole hydrochloride (I): $R_1$=Cl; $R_2$=OCH$_3$; $R_3$=H; $R_4$=CH$_3$; $R_5$=—CH$_2$CH$_2$CH$_3$;

$R_6$ =

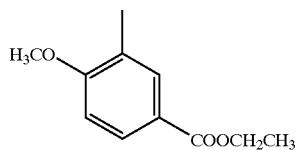

1 g of 4-(2-chloro-4-methoxyphenyl)-5-methyl-2-[N-(5-carboxy-2methoxyphenyl)-N-propylamino]thiazole (EXAMPLE 3) is dissolved at room temperature and under argon in 3 ml of dimethylformamide and then 0.66 g of Cs$_2$CO$_3$ and 0.5 ml of ethyl iodide are added. The reaction mixture is stirred for one hour and then diluted with ethyl acetate. It is washed with water, dried over sodium sulphate and evaporated to dryness. The residue is purified by chromatography on a silica gel column eluted with a cyclohexane/ethyl acetate 5/1 (v/v) mixture. The expected product is obtained in the form of a colourless oil.

It is taken up in dichloromethane and a 0.1 N solution of hydrochloric acid in isopropanol is added. After filtration, the expected product is obtained in the hydrochloride form; m.p.=111° C.

EXAMPLE 5

4-(2-Chloro-4-methoxyphenyl)-5methyl)-2-[N-(92-methoxy-5-morpholinocarbonylphenyl)-N-propylamino]thiazole (I): $R_1$=Cl; $R_2$=OCH$_3$; $R_3$=H; $R_4$=CH$_3$; $R_5$=—CH$_2$CH$_2$CH$_3$;

$R_6$ =

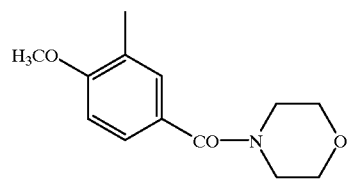

1 g of 4-(2-chloro-4-methoxyphenyl)-5-methyl-2-[N-(5-carboxy-2-methoxyphenyl)-N-propylamino]thiazole (EXAMPLE 3) is added in solution in 19 ml of dimethylformamide, and then 0.31 ml of triethylamine and 0.32 ml of isobutylchloroformate are added at −10° C. and under argon. The reaction mixture is stirred for 10 minutes and 0.8 ml of morpholine is added. The mixture is kept stirring for 2 hours at room temperature. The reaction mixture is then diluted in ethyl acetate, washed with water, dried over sodium sulphate and then evaporated under vacuum. The residue is purified by chromatography on a silica gel column eluted with a cyclohexane/ethyl acetate 1/1 (v/v) mixture. The expected product is obtained in the form of a powder; m.p.=62° C.

EXAMPLE 6

4-(2-Chloro-4-methoxyphenyl)-5-methyl-2-[N-(5-acetyl-2-methoxyphenyl)-N-propylamino]thiazole (I): $R_1$=Cl; $R_2$=OCH$_3$; $R_3$=H; $R_4$=CH$_3$; $R_3$=—CH$_2$CH$_2$CH$_3$;

$R_6$ =

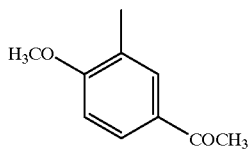

At 0° C., under an inert atmosphere, 2 g of 4-(2-chloro-4-methoxyphenyl)-5-methyl-2-[N-(5-carboxy-2-methoxyphenyl)-N-propylamino]thiazole are dissolved in 30 ml of diethyl ether. Methyllithium (3 equivalents) is slowly added to the ethereal solution. When the addition is complete, the reaction mixture is brought to room temperature. After 2 hours, it is diluted with ethyl acetate and then hydrolyzed. The organic phase is washed with water and then dried over sodium sulphate. After evaporation, the residue is purified on a silica gel. The expected product is obtained in the form of a powder; m.p.=50° C.

EXAMPLE 7

4-(2-Chloro-4-methoxyphenyl)-5-methyl-2-[N-(5-cyclopropylcarbonyl-2-methoxyphenyl)-N-propylamino]thiazole (I): $R_1$=Cl; $R_2$=OCH$_3$; $R_3$=H; $R_4$=CH$_3$; $R_5$=—CH$_2$CH$_2$CH$_3$;

$R_6$ =

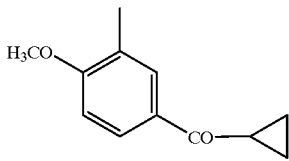

Starting with lithium cyclopropane and using the process of EXAMPLE 6, the expected product is obtained in the form of a powder; m.p.=69° C.

EXAMPLE 8

4-(2-Chloro-4-methoxyphenyl)-5-methyl-2-[N-(5-isobutyryl-2-methoxyphenyl)-N-propylamino]thiazole (I): $R_1$ Cl; $R_2$=OCH$_3$; $R_3$=H; $R_4$=CH$_3$; $R_5$=—CH$_2$CH$_2$CH$_3$;

$R_6$ =

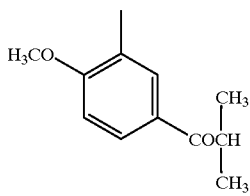

Stage 1: under an inert atmosphere, 6.5 g of 4-(2-chloro-4-methoxyphenyl)-5-methyl-2-[N-(5-carboxy-2-methoxyphenyl)-N-propylamino]thiazole are dissolved in 130 ml of dimethylformamide. The temperature of the mixture is brought to 0° C., 7.5 ml of triethylamine are added as well as 2.8 ml of isobutyl chloroformate (1.5 equivalents). After 15 minutes, 2.84 g of N-methoxy-N-methylamine (2 equivalents) are added. The reaction is practically complete in 2 hours at room temperature.

The reaction mixture is then diluted with ethyl acetate. After several washes with water and then with a saturated NaCl solution, the organic phase is dried over sodium sulphate. After evaporation, the product is purified on a silica gel; eluent dichloromethane/ethyl acetate 95/5 (v/v); yield=72%.

$^1$H NMR (CDCl$_3$): 0.91(t,3H); 1.59(m,2H); 2.04(s,3H); 3.37(s,3H); 3.58(s,3H); 3.81(s,3H); 3.85(m,2H); 3.88(s,3H); 6.81–6.87(dd,1H); 6.97–7.06(m,2H); 7.33–7.38(d,1H); 7.78–7.82(m,2H).

Stage 2: the solution of 650 mg of product previously obtained under an inert atmosphere in 2 ml of tetrahydrofuran is slowly added and at 0° C. over 1.4 ml of a solution (2 M) of isopropylmagnesium chloride in tetrahydrofuran. After a reaction time of 2 hours at room temperature, the reaction mixture is again cooled before being acidified with 1 N hydrochloric acid. The aqueous phase is extracted with diethyl ether. The organic phases are then washed with a satureted sodium bicarbonate solution and then with a saturated sodium chloride solution.

The residue is dried over sodium sulphate, the solvent evaporated off before being purified on a silica gel; eluent cyclohexane (3), ethyl acetate (1). The product is obtained in hydrochloride form; m.p.=114° C.

EXAMPLE 9

4-(2-Chloro-4-methoxyphenyl)-5-methyl-2-[N-(5-hydroxymethyl-2-methoxyphenyl)-N-propylamino]thiazole.

(I): $R_1$=Cl; $R_2$=OCH$_3$; $R_3$=H; $R_4$=CH$_3$; $R_5$=—CH$_2$CH$_2$CH$_3$;

$R_6$ =

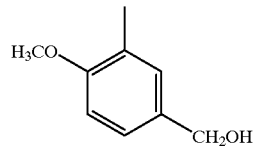

At 0° C., under an inert atmosphere, 1.5 g of 4-(2-chloro-4-methoxyphenyl)-5methyl-2-[N-(5-carboxy-2-methoxyphenyl)-N-propylamino]thiazole are dissolved in 11 ml of tetrahydrofuran. 5 ml of a 1 M solution of lithium aluminium hydride in tetrahydrofuran are added slowly so that the temperature of the mixture does not exceed 10° C. After 2 hours at room temperature, the reaction mixture is cooled with the aid of an ice bath and then hydrolyzed slowly. The crude material is alkalanized before being filtered over sodium sulphate. After evaporation under vacuum, the product is obtained by purification on a silica gel; eluent: dichloro-methane/ethyl acetate 95/5 (v/v); yield=87%. The expected product is in the form of a powder; m.p.=115° C.

EXAMPLE 10

4-(2-Chloro-4-methoxyphenyl)-5-methyl-2-[N-(2-methoxy-5-methoxymethylphenyl)-N-propylamino]thiazole hydrochloride.

(I): $R_1$=Cl; $R_2$=OCH$_3$; $R_3$=H; $R_4$=CH$_3$; $R_5$=—CH$_2$CH$_2$CH$_3$;

$R_6 =$

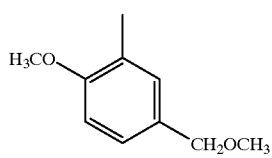

At 0° C., under an inert atmosphere, 320 mg of 4-(2-chloro-4-methoxyphenyl)-5-methyl-2-[N-(5-hydroxymethyl-2-methoxyphenyl)-N-propylamino]thiazole are dissolved in 0.7 ml of dimethylformamide. 70 mg of sodium hydride (50% in oil) are added. After 5 minutes, 0.24 ml of methyl iodide is added. After 12 hours at room temperature, the reaction mixture is diluted with ethyl acetate and then hydrolyzed. The organic phase is washed several times with water before being dried over sodium sulphate. After purification on a silica gel; the expected product is dissolved in dichloromethane. A 0.1 N solution of hydrochloric acid in isopropanol is then added. After evaporation under vacuum, the expected product is obtained in hydrochloride form; m.p.=71° C.

EXAMPLE 11

4-(2-Chloro-4-methoxyphenyl)-5-methyl-2-[N-(5-chloro-2-methylphenyl)-N-propylamino]thiazole hydrochloride.

(I): $R_1$=Cl; $R_2$=OCH$_3$; $R_3$=H; $R_4$=CH$_3$; $R_5$=—CH$_2$CH$_2$CH$_3$;

$R_6 =$

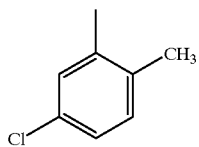

Stage 1: 5 g of 2-bromo1-(2chloro-4-methoxyphenyl)-propan-1-one (Compound 1-2) and 4.2 ml of triethylamine in 25 ml of ethanol are added to 3 g of N-(5-chloro-2-methylphenyl)thiourea (Compound 11-1) in 25 ml of ethanol. The reaction mixture is heated under reflux for 2 hours and reduced under vacuum. The residue thus obtained is taken up in dichloromethane. The resulting solution is washed with water, dried over sodium sulphate and evaporated off. 5.09 g of the expected crude product are obtained.

$^1$H NMR (CDCl$_3$): 2.14(s,3H); 2.23(s,3H); 3.80(s,3H); 6.80–7.34(m,l6H); 9.02(m,1H).

Stage 2: 5.09 g of the crude product previously obtained are dissolved in 70 ml of anhydrous dimethylformamide and 1.08 g of sodium hydride are added under argon. After stirring for 15 minutes, 4.4 g of propyl iodide are added and the reaction mixture is heated at 75° C. for 2 hours. It is evaporated, the residue obtained hydrolyzed and the aqueous phase extracted with ethyl acetate. The organic phase is washed with a saturated NaCl solution, dried over sodium sulphate and evaporated under vacuum. The residue is purified by chromatography on a silica gel column, eluted with a cyclohexane/ethyl acetate 20/1 (v/v) mixture.

The product obtained is taken up in dichloromethane and a 0.1 N solution of hydrochloric acid in isopropanol is added so as to obtain the hydrochloride; m.p.=69° C.

EXAMPLE 12

4-(2-Chloro-4-methoxyphenyl)-5-methyl-2-[N-(3,5-dimethylphenyl)-N-propylamino]thiazole (I): $R_1$=Cl; $R_2$=OCH$_3$; $R_3$=H; $R_4$=CH$_3$; $R_5$=—CH$_2$CH$_2$CH$_3$;

$R_6 =$

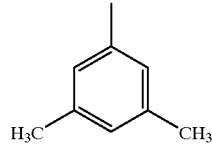

By carrying out the procedure according to EXAMPLE 11

4-(2-chloro-4-methoxyphenyl)-5-methyl-2-[N-(3,5-dimethylphenyl)-N-propylamino]thiazole is obtained, with the same reagents but at room temperature as regards the reaction temperature after introducing propyl iodide.

The product obtained is in the form of a powder; m.p.=40° C.

EXAMPLE 13

4-(2-Chloro-4-methoxyphenyl)-5-methyl-2-[N-(2-methoxy-5-o-tolylphenyl)-N-propylamino]thiazole.

(I): $R_1$=Cl; $R_2$=OCH$_3$; $R_3$=H; $R_4$=CH$_3$; $R_5$=—CH$_2$CH$_2$CH$_3$;

$R_6 =$

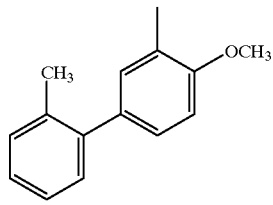

1.96 g of barium hydroxide, 0.52 g of o-tolyl-boronic acid and 40 mg of palladium diacetate are added in succession to 1 g of 4-(2-chloro-4-methoxyphenyl)-5-methyl-2-[N-(5-bromo-2-methoxyphenyl)-N-propylamino]thiazole, in solution in 25 ml of ethanol and 0.8 ml of water. The reaction mixture is heated for 1 hour under reflux; after returning to room temperature, it is filtered on Celite. After evaporation of the solvent, the residue is taken up in dichloromethane. The organic phase is washed with water and then dried over sodium sulphate. The evaporation residue is purified on silica gel; eluent dichloromethane/cyclohexane 9/1 (v/v). The expected product is obtained in the form of a powder; m.p.=55° C.

EXAMPLE 14

4-(2-Chloro-4-methoxyphenyl)-5-methyl-2-[N-(2-methoxy-5-nitrophenyl)-N-propylamino]thiazole (I): $R_1$=Cl; $R_2$=OCH$_3$; $R_3$=H; $R_4$=CH$_3$; $R_5$=—CH$_2$CH$_2$CH$_3$;

$R_6 =$

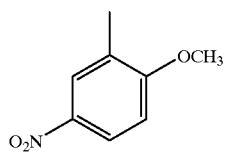

By carrying out the procedure according to EXAMPLE 12 and by using 2-bromo-1-(2-chloro-4-methoxyphenyl)propan-1-one (Compound 1-2) and N-(2-methoxy-5-nitrophenyl)-N-propylthiourea, the expected product is obtained in the form of a powder; m.p.=97° C.

EXAMPLE 15

4-(2-Chloro-4-methoxyphenyl)-5-methyl-2-[N-(5-amino-2-methoxyphenyl)-N-propylamino]thiazole.

(I): $R_1=Cl$; $R_2=OCH_3$; $R_3=H$; $R_4=CH_3$; $R_5=-CH_2CH_2CH_3$;

$R_6 =$

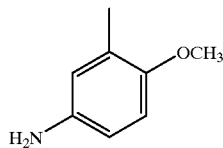

13.5 g of 4-(2-chloro-4-methoxyphenyl)-5-methyl-2-[N-(2-methoxy-5-nitrophenyl)-N-propylamino]thiazole are dissolved in 120 ml of methanol and then 5.3 g of iron powder and 18.5 ml of concentrated hydrochloric acid are added. The mixture is heated under reflux for half an hour. The methanol is evaporated under vacuum, the residue is taken up in dichloromethane before being filtered on Celite. The product is extracted with 1 N hydrochloric acid. The acidic phase is then neutralized with sodium hydroxide before being extracted with dichloromethane. After evaporation of the dichloromethane, the crude reaction product is purified on silica gel; eluent dichloromethane/methanol 95/5 (v/v).

The expected product is solid; m.p.=89° C.

EXAMPLE 16

4-(2-Chloro-4-methoxyphenyl)-5methyl-2[N-(5-acetamido-2-methoxyphenyl)-N-propylamino]thiazole (I): $R_1=Cl$; $R_2=OCH_3$; $R_3=H$; $R_4=CH_3$; $R_5=-CH_2CH_2CH_3$;

$R_6 =$

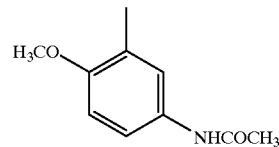

At 0° C., under an inert atmosphere, 1 g of 4-(2-chloro-4-methoxyphenyl)-5-methyl-2-[N-(5-amino-2-methoxyphenyl)-N-propylamino]thiazole is dissolved in 3.5 ml of dichloromethane. 0.4 ml of triethylamine is added followed by 0.14 ml of acetyl bromide. After 1 hour at room temperature, the reaction mixture is diluted with dichloromethane. The organic phase is washed with water and then dried over sodium sulphate. The evaporation residue is purified on silica gel; eluent cyclohexane/ethyl acetate 1/1.

The product solidifies in pentane; yield=71%; m.p.=171° C.

EXAMPLE 17

4-(2,4,6-Trichlorophenyl)-5methyl-2[N-(2,5-ditrifluoromethylphenyl)-N-propylamino]thiazole (I): $R_1=Cl$; $R_2=Cl$; $R_3=Cl$; $R_4=CH_3$; $R_5=-CH_2CH_2CH_3$;

$R_6 =$

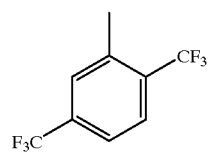

Stage 1: by carrying out the procedure according to EXAMPLE 2, using 2-bromo-1-(2,4,6-trichlorophenyl)-ethan-1-one (Compound 3-1) and N-(2,5-ditrifluoromethylphenyl)-N-propylthiourea, 4-(2,4,6-trichlorophenyl)-2-[N-(2,5-ditrifluoromethylphenyl)-N-propylamino]thiazole is obtained; yield=33%.

$^1$H NMR (CDCl$_3$): 0.87(t,3H, J=3.8); 1.77(sext., 2H, J=3.8, J=7.8); 3.88(m,2H); 6.51(s,1H); 7.36(s,2H).

Stage 2: the product previously obtained is dissolved in 50 ml of dichloromethane. 0.3 ml of triethylamine is added followed by 0.11 ml of bromine. The mixture is stirred for 8 hours and a solution of sodium thiosulphate is added. The aqueous phase is extracted with dichloromethane. The organic phases are combined, washed with water and dried over sodium sulphate. The evaporation residue is purified on silica; eluent dichloromethane/cyclohexane 1/2.

$^1$H NMR (CDCl$_3$): 0.92(t,3H, J=3.7); 1.73(sext., 2H, J=3.7, J=7.7); 3.71(m,2H); 7.38(s,2H); 7.72(s,1H); 7.80(d, 1H, J=4.2); 796(d,1H, J=4.2).

Stage 3: the product derived from Stage 2 (1.05 g) is dissolved in 40 ml of tetrahydrofuran. At −70° C., under an inert atmosphere, 1.6 ml of butyllithium (1.6 M in hexane) are added. After 20 minutes, 0.7 ml of methyl iodide (6 equivalents) is added. The mixtue, after gradually returning to room temperature, is stirred for 3 hours. The mixture is then hydrolyzed at low temperature. The aqueous phase is extracted with dichloromethane, the organic phases are combined and dried over sodium sulphate. The evaporation residue is purified on silica gel; eluent dichloromethane/cyclohexane 1/2. The product is obtained in the form of a powder; m.p.=88° C.

By carrying out the procedure according to EXAMPLES 1 to 17 above, EXAMPLES 18 to 75, described in TABLE I below, are prepared in the same manner:

TABLE I

[Structure: 5-methyl-thiazole with N(CH2CH2CH3)(R5) at 2-position, and phenyl substituted with R1, R2, R3 at 4-position (1)]

| Example number | R₁ | R₂ | R₃ | R₄ | Route | m.p.; °C. salt |
|---|---|---|---|---|---|---|
| 18 | Cl | OCH₃ | H | 2-Cl-phenyl | B | 58 HCl |
| 19 | Cl | OCH₃ | H | 3-Cl-phenyl | B | 69 HCl |
| 20 | Cl | OCH₃ | H | 2-CH₃-phenyl | B | 83 base |
| 21 | Cl | OCH₃ | H | 2-CF₃-phenyl | A | 172 HCl |
| 22 | Cl | OCH₃ | H | 2-OCH₃-phenyl | B | 85 base |
| 23 | Cl | OCH₃ | H | 2-OCF₃-phenyl | B | 45 base |
| 24 | Cl | OCH₃ | H | 2,4-diCl-phenyl | B | 105 HCl |

TABLE I-continued
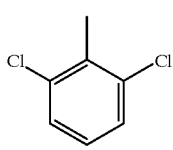
(1)
| Example number | R₁ | R₂ | R₃ | R₄ | Route | m.p.; °C. salt |
|---|---|---|---|---|---|---|
| 25 | Cl | OCH₃ | H | 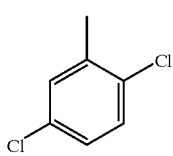 | B | 98 base |
| 26 | Cl | OCH₃ | H | 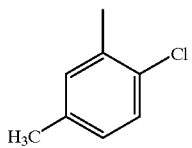 | B | 68 HCl |
| 27 | Cl | OCH₃ | H | 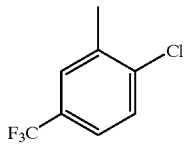 | B | 170 HCl |
| 28 | Cl | OCH₃ | H | 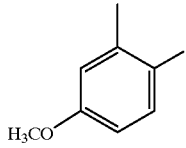 | B | 60 HCl |
| 29 | Cl | OCH₃ | H | 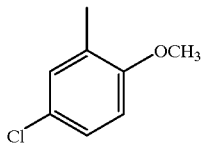 | B | 172 HCl |
| 30 | Cl | OCH₃ | H | 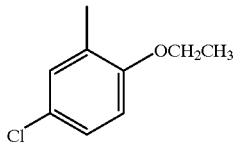 | B | 65 HCl |
| 31 | Cl | OCH₃ | H |  | B | 109 HCl |

TABLE I-continued
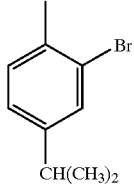
(1)
| Example number | R₁ | R₂ | R₃ | R₄ | Route | m.p.; °C. salt |
|---|---|---|---|---|---|---|
| 32 | Cl | OCH₃ | H | 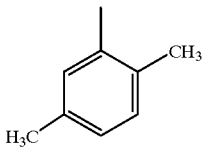 | A | 90 HCl |
| 33 | Cl | OCH₃ | H | 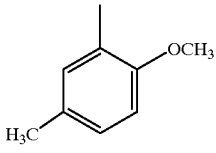 | B | 47 sulphonate |
| 34 | Cl | OCH₃ | H | 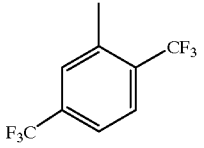 | B | NMR$^{(1)}$ oil |
| 35 | Cl | OCH₃ | H | 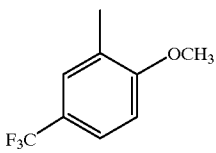 | B | NMR$^{(2)}$ oil |
| 36 | Cl | OCH₃ | H | 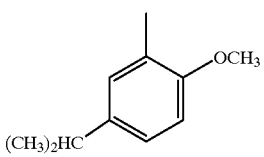 | B | 94 HCl |
| 37 | Cl | OCH₃ | H | 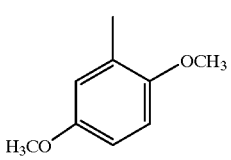 | A | 98 HCl |
| 38 | Cl | OCH₃ | H |  | B | 68 HCl |

TABLE I-continued

Structure (1): 4-aryl-5-methyl-2-(N-propyl-N-R5-amino)thiazole with aryl bearing R1 (ortho), R2 (para), R3 (meta) substituents.

| Example number | R₁ | R₂ | R₃ | R₄ | Route | m.p.; °C. salt |
|---|---|---|---|---|---|---|
| 39 | Cl | OCH₃ | H | 4-methoxy-3-methylphenyl with COOCH₃ | B | 82 HCl |
| 40 | Cl | OCH₃ | H | 2,4,6-trichloro-3-methylphenyl | B | 60 base |
| 41 | Cl | Cl | H | 2,5-dichloro-3-methylphenyl | B | 85 base |
| 42 | Cl | OCH₃ | H | 6-methoxy-5-methyl-1,2,3,4-tetrahydronaphthyl | A | 91 HCl |
| 43 | Cl | OCH₃ | H | 4-methoxy-3-methyl-biphenyl | B | 71 base |
| 44 | Cl | OCH₃ | H | 2,6-dimethoxy-3-methylphenyl (H₃CO, OCH₃) | B | 120 base |
| 45 | Cl | OCH₃ | H | 3-methoxy-2,6-dimethylphenyl | B | 203 HCl |

TABLE I-continued

Structure (1): 5-methyl-4-aryl-2-(N-propyl-N-R5-amino)thiazole with aryl substituents R1 (ortho), R2 (para), R3 (meta).

| Example number | R₁ | R₂ | R₃ | R₄ | Route | m.p.; °C. salt |
|---|---|---|---|---|---|---|
| 46 | Cl | OCH₃ | H | 4-methoxy-3-methyl-phenyl with CH₂CH₃ | B | 109 HCl |
| 47 | Cl | OCH₃ | H | 5-chloro-2,4-dimethoxy-phenyl with methyl | B | 61 base |
| 48 | Cl | OCH₃ | H | 4-chloro-2,5-dimethoxy-phenyl with methyl | B | 71 base |
| 49 | Cl | OCH₃ | H | 4-bromo-2-methoxy-phenyl with methyl | B | 85 base |
| 50 | Cl | OCH₃ | H | 5-chloro-2-methoxy-4-methyl-benzoic acid | B | 180 base |
| 51 | Cl | OCH₃ | H | methyl 5-chloro-2-methoxy-4-methyl-benzoate | B | 78 HCl |

TABLE I-continued

| Example number | R₁ | R₂ | R₃ | R₄ | Route | m.p.; °C. salt |
|---|---|---|---|---|---|---|
| 52 | Cl | OCH₃ | H | 4-methyl-5-chloro-2-methoxy-phenyl with COOCH₂CH₃ | B | 62 HCl |
| 53 | Cl | OCH₃ | H | 2,3-dimethylphenyl | A | 96 HCl |
| 54 | Cl | OCH₃ | H | 2,6-diethyl-3-methylphenyl | A | 180 HCl |
| 55 | Cl | OCH₃ | H | 4-methoxy-3-methylphenyl with CO(CH₂)₂CH₃ | B | 80 HCl |
| 56 | Cl | OCH₃ | H | 2,3-dichloro-6-methylphenyl | A | 80 base |
| 57 | Cl | OCH₃ | H | 4-methoxy-3-methylphenyl with COCH₂CH₃ | B | 65 HCl |
| 58 | Cl | OCH₃ | H | 4-methoxy-3-methylphenyl benzoyl | B | 53 base |

TABLE I-continued

[Structure (1): 5-methyl-4-(substituted phenyl with R1, R2, R3)-thiazole-2-yl-N(CH2CH2CH3)(R5)]

| Example number | R₁ | R₂ | R₃ | R₄ | Route | m.p.; °C. salt |
|---|---|---|---|---|---|---|
| 59 | Cl | Cl | H | 2-CF₃-5-CF₃-phenyl (with CH₃) | B | ¹HNMR⁽³⁾ oil |
| 60 | Cl | OCH₃ | H | 2,6-dichloro-3-methylphenyl | A | 158 HCl |
| 61 | Cl | Cl | H | 2,6-dichloro-3-methylphenyl | A | 77 base |
| 62 | Cl | Cl | H | 2,6-dimethyl-3-methoxyphenyl | B | 79 base |
| 63 | Cl | Cl | H | 4-chloro-2,6-dimethylphenyl | A | 59 HCl |
| 64 | Cl | CF₃ | H | 4-chloro-2-methylphenyl (with CH₃) | A | ¹HNMR⁽⁴⁾ oil |
| 65 | Cl | OCH₃ | H | 2-chloro-3,5-difluoro-methylphenyl | A | 56 HCl |

TABLE I-continued

Structure (1):

2-[N-ethyl-N-propyl-N-R₅]-4-(substituted phenyl)-5-methylthiazole, where the phenyl bears R₁ (ortho), R₂ (para), R₃ (meta)

| Example number | R₁ | R₂ | R₃ | R₄ | Route | m.p.; °C. salt |
|---|---|---|---|---|---|---|
| 66 | Cl | Cl | 5-Cl | 6-methoxy-5-methyl-1,2,3,4-tetrahydronaphthalen-?-yl | A | 101 HCl |
| 67 | Cl | Cl | 5-Cl | 6,7-dimethyl-4H-1,3-benzodioxin-?-yl | A | 96 HCl |
| 68 | Cl | OCH₃ | 5-CH₃ | 4-methoxy-3,?-dimethylphenyl (2-CH₃, 4-OCH₃, 5-CH₃) | B | 104 base |
| 69 | Cl | OCH₃ | H | 4-(trifluoromethyl)-2-methyl-1-(methylthio)phenyl | B | 69 HCl |
| 70 | Cl | Cl | 5-CH₃ | 4-methoxy-3-methyl-?-methylphenyl | B | 76 HCl |
| 71 | Cl | CH₃ | 5-CH₃ | 4-methoxy-3,?-dimethylphenyl | B | 79 HCl |
| 72 | Cl | Cl | H | 4-methoxy-3,?-dimethylphenyl | B | 166 HCl |

TABLE I-continued

[Structure (1): thiazole with H3C, S, N-CH2CH2CH3, R5, N, phenyl with R1, R2, R3]

(1)

| Example number | R1 | R2 | R3 | R4 | Route | m.p.; °C. salt |
|---|---|---|---|---|---|---|
| 73 | Cl | OCH3 | H | [H3C-phenyl-COOCH3] | B | 77 HCl |
| 74 | Cl | OCH3 | H | [H3CO-methyl-tetrahydronaphthalene] | A | 96 HCl |
| 75 | Cl | Cl | 5-Cl | [H3CO-methyl-tetrahydronaphthalene] | A | 82 HCl |

(1) $^1$H NMR (CDCl$_3$): 0.89(t, 3H); 1.59(m, 2H); 2.09(s, 3H); 2.30(s, 3H); 3.80(m, 8H); 6.79–7.37(m, 6H);
(2) $^1$H NMR (CDCl$_3$): 0.90(t, 3H); 1.77(m, 2H); 2.09(s, 3H); 3.79(m, 5H); 6.79–7.94(m, 6H);
(3) $^1$H NMR (CDCl$_3$): 0.91(t, 3H); 1.75(m, 2H); 2.09(s, 3H); 3.73(m, 2H); 7.22–7.35(m, 2H); 7.44(d, 1H); 7.67–7.74(m, 2H); 7.90–7.95(m, 1H)
(4) $^1$H NMR (CDCl$_3$): 0.92(t, 3H); 1.66(m, 2H); 2.08(s, 3H); 2.25(s, 3H); 3.75(m, 2H); 7.25–7.28(m, 3H); 7.55(m, 2H); 7.70(m, 1H).

EXAMPLE 76

4-(2-Chloro-4-methoxyphenyl)-5-methyl-2-[N-(5-chloro-2-methylphenyl)-N-prop-2-ynylamino] thiazole hydrobromide (I): R$_1$=Cl; R$_2$=OCH$_3$; R$_3$=H; R$_4$=CH$_3$; R$_5$=—CH$_2$—C≡CH

R$_6$ =

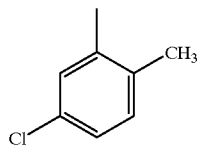

Stage 1: By carrying out the procedure according to EXAMPLE 11 but using 2-propynyl iodide in Stage 2,4-(2-chloro-4methoxyphenyl)-5-methyl-2-[N-(5-chloro-2-methylphenyl)amino]thiazole is obtained.

Stage 2: At 0° C., under argon, 1.3 g of the product obtained in Stage 1 are dissolved in 10 ml of dimethylformamide. 0.2 g of sodium hydride (50% in oil) is added. After a quarter of an hour, 0.8 ml of an 80% solution of propargyl bromide in toluene is added slowly. The reaction mixture is stirred. The reaction mixture is diluted with ethyl acetate and it is hydrolyzed.

The organic phase is washed 3 times with water and then dried over sodium sulphate. After evaporation, the product is purified on a silica gel; eluent cyclohexane, dichloromethane/ethyl acetate 80/20 (v/v) mixture. The hydrobromide is obtained by adding the product previously obtained, in solution in dichloromethane, to a 0.2 M solution of hydrobromic acid in isopropanol. After evaporation, a white powder is obtained; m.p.=101° C.

What is claimed is:
1. A method for the treatment of diseases requiring modulation of the action of corticotropin releasing factor which comprises administering to a patient in need of such treatment an effective amount of a compound of formula:

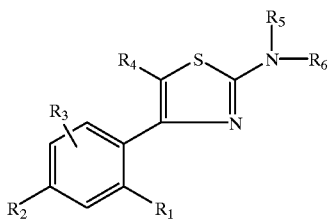

(I)

in which
- R$_1$ and R$_2$, which are identical or different, each represent independently a halogen atom; a (C$_1$–C$_5$)hydroxyalkyl; a (C$_1$–C$_5$)alkyl; an aralkyl in which the aryl part is a (C$_6$–C$_8$) and the alkyl part is a (C$_1$–C$_4$); a (C$_1$–C$_5$) alkoxy; a trifluoromethyl group; a nitro group; a nitrile group; a group —SR in which R represents hydrogen, a (C$_1$–C$_5$)alkyl or an aralkyl in which the aryl part is a (C$_6$–C$_8$) and the alkyl part is a (C$_1$–C$_4$); a group —S—CO—R° in which R° represents a (C$_1$–C$_5$)alkyl radical or an aralkyl in which the aryl part is a (C$_6$–C$_8$) and the alkyl part is a (C$_1$–C$_4$); a group —COORa in which Ra represents hydrogen or a (C$_1$–C$_5$)alkyl; a group —CONRaRb with Ra and Rb as defined above for Ra; a group —NRaRb with Ra and Rb as defined above for Ra; a group —CONRcRd or —NRcRd in which Rc and Rd constitute, with the nitrogen atom to which they are attached, a 5- to 7-membered heterocycle; or a group —NHCO—NRaRb with Ra and Rb as defined above for Ra;
- R$_3$ represents hydrogen or is as defined above for R$_1$ and R$_2$;
- R$_4$ represents a (C$_1$–C$_5$)alkyl; a hydroxymethyl group; a formyl group; or a halogen atom;
- R$_5$ represents a (C$_1$–C$_5$)alkyl; a cycloalklyalkyl group in which the cycloalkyl is a (C$_3$–C$_7$) and the alkyl is a (C$_1$–C$_5$); an alkenyl of 3 to 6 carbon atoms; a (C$_1$–C$_5$) hydroxyalkyl; an alkylcarbonyloxyalkyl group in which the alkyls are a (C$_1$–C$_5$); or an alkynyl group of 3 to 6 carbon atoms;
- R$_6$ represents a phenyl substituted with one or more substituents Z as defined below; a monocyclic heteroaromatic C$_5$–C$_7$ group substituted with one or more radicals Z as defined below; or a bicyclic C$_9$–C$_{10}$ group consisting of an aromatic monocycle optionally comprising one or more heteroatoms selected from O, N and S, condensed with a cycloalkyl group optionally comprising in the ring one or more heteroatoms selected from O, N and S, which bicyclic group is substituted with one or more substituents Z as defined below and which is attched to the nitrogen by the ring of an aromatic nature, it being understood that R$_6$ does not represent a substituted indan and that the substituent Z represents a radical selected from: a halogen atom, a nitro group, a hydroxyl group, a trifluoromethyl group, a (C$_1$–C$_5$)alkyl, a (C$_1$–C$_5$)thioalkyl, a group —NRaRb with Ra and Rb as defined above for Ra, a (C$_1$–C$_5$)hydroxyalkyl, a (C$_1$–C$_5$)alkoxy, a trifluoromethyloxy group, an alkoxyalkyl in which the alkyls are a (C$_1$–C$_5$), a group —COORa with Ra as defined above, a group —CONRaRb with Ra and Rb as defined above for Ra, a carboxy(C$_1$–C$_5$)alkyl, an alkoxycarbonylalkyl in which the alkyls are a (C$_1$–C$_5$), a (C$_1$–C$_5$) alkylcarbonyl, an alkylcarbonylalkyl in which the alkyls are a (C$_1$–C$_5$), a morpholinocarbonyl or morpholinocarbonyl(C$_1$–C$_5$)alkyl group, or a group —NRaCOORb with Ra and Rb as defined above, a group —NHCORe in which Re represents a (C$_1$–C$_5$) alkyl, a cycloalkylcarbonyl in which the cycloalkyl is a (C$_3$–C$_6$), a cycloalkylalkylcarbonyl in which the cycloalkyl is a (C$_3$–C$_6$) and the alkyl a (C$_1$–C$_3$), a benzoyl, a phenyl which is unsubstituted or substituted with a (C$_1$–C$_5$)alkyl, with a (C$_1$–C$_5$)alkoxy, with a halogen atom, with a nitro group, with a hydroxyl group or with a trifluoromethyl group;

their stereoisomers, their addition salts, their hydrates and/or their solvates.

2. A method according to claim 1 in which R$_6$ represents a phenyl or tetrahydronaphthyl group substituted with one or more substituents Z as defined for (I), R$_1$, R$_2$, R$_3$, R$_4$, and R$_5$ also being as defined for (I), one of their stereoisomers, one of their salts, one of their hydrates and/or one of their solvates.

3. A method according to claim 2 in which R$_4$ represents a methyl, R$_1$, R$_2$, R$_3$ and R$_5$ being as defined for (I), one of their stereoisomers, one of their hydrates and/or one of their solvates.

4. A method according to claim 3 in which R$_1$ and/or R$_2$ represents a halogen, a trifluoromethyl, a (C$_1$–C$_5$)alkyl or a (C$_1$–C$_5$)alkoxy, R$_4$ represents a methyl, R$_6$ represents a phenyl at least substituted at the 2 position with a substituent Z as defined for (I), R$_3$ and R$_5$ are as defined for (I), one of their stereoisomers, one of their salts, one of their hydrates and/or one of their solvates.

5. A method according to claim 1 wherein the compound is selected from
- 4-(2-Chloro-4-methoxyphenyl)-5-methyl-2-[N-(5-ethoxycarbonyl-2-methoxyphenyl)-N-propylamino]thiazole
- 4-(2-Chloro-4-methoxyphenyl)-5-methyl-2-[N-(5-chloro-2-methylphenyl)-N-propylamino]thiazole
- 4-(2-Chloro-4-methoxyphenyl)-5-methyl-2-[N-(2-trifluoromethylphenyl)-N-propylamino]thiazole
- 4-(2-Chloro-4-methoxyphenyl)-5-methyl-2-[N-(2-methoxyphenyl)-N-propylamino]thiazole
- 4-(2-Chloro-4-methoxyphenyl)-5-methyl-2-[N-(2,6-dichlorophenyl)-N-propylamino]thiazole
- 4-(2-Chloro-4-methoxyphenyl)-5-methyl-2-[N-(2,5-dichlorophenyl)-N-propylamino]thiazole
- 4-(2-Chloro-4-methoxyphenyl)-5-methyl-2-[N-(2-chloro-5-methylphenyl)-N-propylamino]thiazole
- 4-(2-Chloro-4-methoxyphenyl)-5-methyl-2-[N-(2-chloro-5-trifluoromethylphenyl)-N-propylamino]thiazole
- 4-(2-Chloro-4-methoxyphenyl)-5-methyl-2-[N-(2-chloro-5-methoxyphenyl)-N-propylamino]thiazole
- 4-(2-Chloro-4-methoxyphenyl)-5-methyl-2-[N-(5-chloro-2-methoxyphenyl)-N-propylamino]thiazole
- 4-(2-Chloro-4-methoxyphenyl)-5-methyl-2-[N-(5-chloro-2-ethoxyphenyl)-N-propylamino]thiazole
- 4-(2-Chloro-4-methoxyphenyl)-5-methyl-2-[N-(2-methoxy-5-methylphenyl)-N-propylamino]thiazole
- 4-(2-Chloro-4-methoxyphenyl)-5-methyl-2-[N-(2,5-dimethylphenyl)-N-propylamino]thiazole
- 4-(2-Chloro-4-methoxyphenyl)-5-methyl-2-[N-(2,5-difluoromethylphenyl)-N-propylamino]thiazole
- 4-(2-Chloro-4-methoxyphenyl)-5-methyl-2-[N-(2-methoxy-5-trifluoromethylphenyl)-N-propylamino]thiazole 4-(2-Chloro-4-methoxyphenyl)-5-methyl-2-[N-(2,5-dimethoxyphenyl)-N-propylamino]thiazole 4-(2-Chloro-4-methoxyphenyl)-5-methyl-2-[N-(2-methoxy-5-methoxycarbonylphenyl)-N-propylamino]thiazole 4-(2,4-Dichlorophenyl)-5-methyl-2-[N-(2,5-dichlorophenyl)-N-propylamino]thiazole 4-(2-Chloro-4-methoxyphenyl)-5-methyl-2-[N-(5-acetyl-2-methoxyphenyl)-N-propylamino]thiazole 4-(2-Chloro-4-methoxyphenyl)-5-methyl-2-[N-(2-(methoxy)-5-(phenyl)phenyl-N-propylamino]thiazole 4-(2-Chloro-4-methoxyphenyl)-5-methyl-2-[N-(2,6-dimethoxyphenyl)-N-propylamino]thiazole 4-(2-Chloro-4-methoxyphenyl)-5-methyl-2-[N-(2-methoxy-6-methylphenyl)-N-propylamino]thiazole 4-(2,4-Dichlorophenyl)-5-methyl-2-[N-(2-methoxy-6-methylphenyl)-N-propylamino]thiazole 4-(2-Chloro-4-methoxyphenyl)-5-methyl-2-[N-(5-ethyl-2-methoxyphenyl)-N-propylamino]thiazole 4-(2-Chloro-4-methoxyphenyl)-5-methyl-2-[N-(5-bromo-2-methoxyphenyl)-N-propylamino]thiazole 4-(2-Chloro-4-methoxyphenyl)-5-methyl-2-[N-(2-methoxy-5-o-tolylphenyl)-N-propylamino]thiazole 4-(2,4,6-Trichlorophenyl)-5-methyl-2-[N-2,5-ditrifluoromethylphenyl)-N-propylamino]thiazole 4-(2,4-Dichlorophenyl)-5-methyl-2-[N-(2,5-ditrifluoromethylphenyl)-N-propylamino]thiazole 4-(2,4-Chloro-4-methoxyphenyl)-5-methyl-2-[N-(2-methoxy-5-nitrophenyl)-N-propylamino]thiazole 4-(2,4-Dichlorophenyl)-5-methyl-2-[N-(2,6-dichloro-5-methylphenyl)-N-propylamino]thiazole 4-(2-Dichlorophenyl)-5-methyl-2-[N-(2-methoxy-6-methylphenyl)-N-propylamino]thiazole 4-(2,4-Dichlorophenyl)-5-methyl-2-[N-(5-chloro-2-methylphenyl)-N-propylamino]thiazole 4-(4-Chloro-2-trifluoromethylphenyl)-5-methyl-2-[N-(5-chloro-2-methylphenyl)-N-propylamino]thiazole 4-(2-Chloro-4-methoxy-5-methylphenyl)-5-methyl-2-[N-(2-methoxy-5-methylphenyl)-N-propylamino]thiazole 4-(2-Chloro-4-methoxyphenyl)-5-methyl-2-[N-(2-methylthio-5-trifluoromethylphenyl)-N-propylamino]thiazole 4-(2,4-Dichloro-5-methylphenyl)-5-methyl-2-[N-(2-methoxy-5-methylphenyl)-N-propylamino]thiazole 4-(2-Chloro-4,5-dimethylphenyl)-5-methyl-2-[N-(2-methoxy-5-methylphenyl)-N-propylamino]thiazole 4-(2-Chloro-4-methoxyphenyl)-5-methyl-2-[N-(2-methoxy-5-methoxycarbonylphenyl)-N-propylamino]thiazole 4-(2-Chloro-4-methoxyphenyl)-5-methyl-2-[N-(5-chloro-2-methylphenyl)-N-prop-2-ynylamino]thiazole one of their stereoisomers, one of their salts, one of their hydrates and/or one of their solvates.

* * * * *